US012577479B2

(12) United States Patent
Ricoult

(10) Patent No.: US 12,577,479 B2
(45) Date of Patent: Mar. 17, 2026

(54) WAX-MICROSPHERE MATRIX COMPOSITIONS AND METHODS OF MAKING AND USING THE SAME

(71) Applicant: ILLUMINA CAMBRIDGE LIMITED, Cambridge (GB)

(72) Inventor: Sébastien Ricoult, Sawston (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 598 days.

(21) Appl. No.: 18/068,868

(22) Filed: Dec. 20, 2022

(65) Prior Publication Data

US 2023/0193147 A1     Jun. 22, 2023

Related U.S. Application Data

(60) Provisional application No. 63/292,185, filed on Dec. 21, 2021.

(51) Int. Cl.
| | |
|---|---|
| *C12Q 1/68* | (2018.01) |
| *C08L 91/06* | (2006.01) |
| *C10G 73/40* | (2006.01) |
| *C12Q 1/6848* | (2018.01) |

(52) U.S. Cl.
CPC .............. *C10G 73/40* (2013.01); *C08L 91/06* (2013.01); *C12Q 1/6848* (2013.01)

(58) Field of Classification Search
CPC ..................................................... C12Q 1/68
USPC ......................................................... 435/6.1
See application file for complete search history.

(56) References Cited

U.S. PATENT DOCUMENTS

| | | | |
|---|---|---|---|
| 5,643,764 A | 7/1997 | Kosak et al. | |
| 2020/0216884 A1* | 7/2020 | O'Farrell | .......... B01L 3/502761 |

FOREIGN PATENT DOCUMENTS

| | | | |
|---|---|---|---|
| EP | 3505933 A1 | 7/2019 |
| WO | 9417106 A1 | 8/1994 |
| WO | 9617083 A1 | 6/1996 |
| WO | 2005110369 A2 | 11/2005 |
| WO | 2006003439 A2 | 1/2006 |

(Continued)

*Primary Examiner* — Aaron A Priest
(74) *Attorney, Agent, or Firm* — Heslin Rothenberg Farley & Mesiti P.C.

(57) ABSTRACT

The present disclosure relates to a method including exposing a composition comprising a wax-microsphere matrix to a first melt-condition, wherein said wax-microsphere matrix comprises a wax component and a plurality of lyophilised microspheres, wherein said plurality of lyophilised microspheres comprise one or more reagent, whereby exposing said composition comprising said wax-microsphere matrix to said first melt-condition melts the wax component; exposing said composition to a first release-condition to rehydrate at least one lyophilised microsphere; and exposing said at least one rehydrated lyophilised microsphere to a separation-condition to separate said wax component from said at least one rehydrated lyophilised microsphere. Also disclosed are methods of preparing a wax-microsphere matrix and releasing one or more reagent from a wax-microsphere matrix as well as compositions. Also disclosed are cartridges with a reagent reservoir including the compositions described herein. Also disclosed are systems for controlling release of one or more reagent including the compositions described herein.

19 Claims, 13 Drawing Sheets

Mitigation with wax slugs

(56) References Cited

FOREIGN PATENT DOCUMENTS

| WO | 2010142960 | A1 | 12/2010 |
| WO | 2015195597 | A1 | 12/2015 |
| WO | 2022221368 | A1 | 10/2022 |

* cited by examiner

Dispensing of current state
microspheres

Mitigation with wax slugs

Stirred heated tub of wax and microspheres

Spray nozzle

Cooling gravity chamber

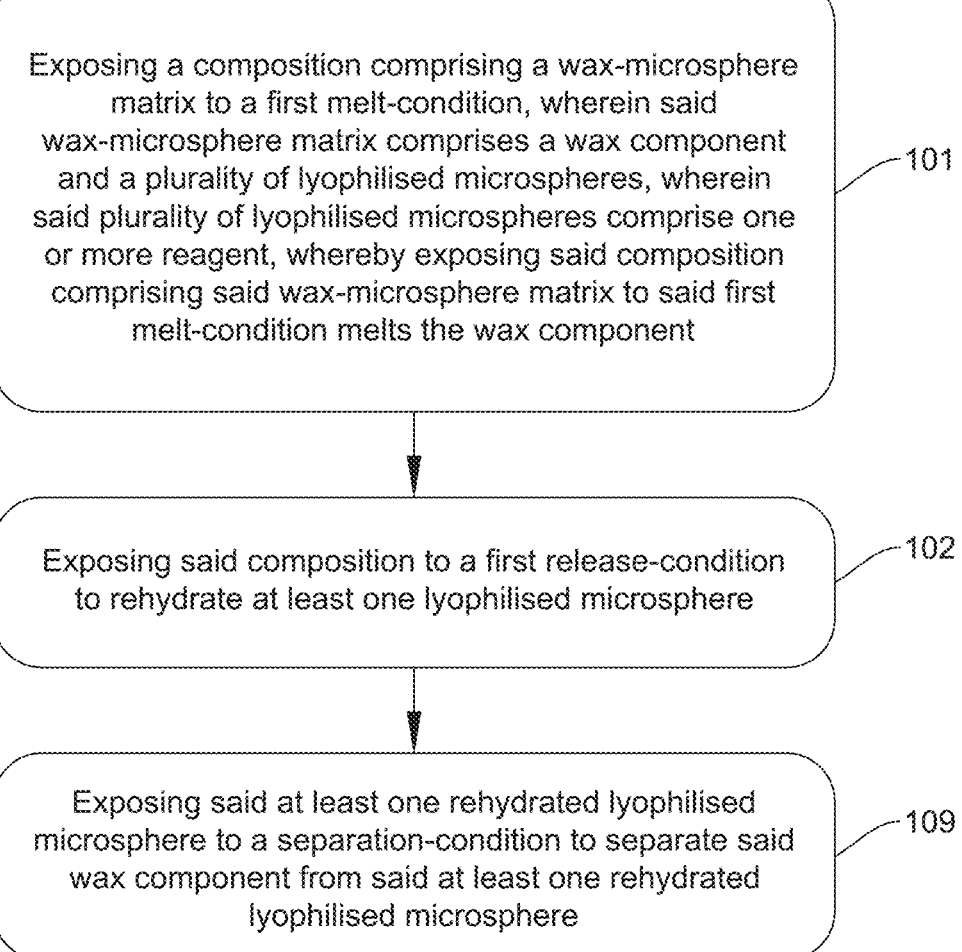

Exposing a composition comprising a wax-microsphere matrix to a first melt-condition, wherein said wax-microsphere matrix comprises a wax component and a plurality of lyophilised microspheres, wherein said plurality of lyophilised microspheres comprise one or more reagent, whereby exposing said composition comprising said wax-microsphere matrix to said first melt-condition melts the wax component — 101

Exposing said composition to a first release-condition to rehydrate at least one lyophilised microsphere — 102

Exposing said at least one rehydrated lyophilised microsphere to a separation-condition to separate said wax component from said at least one rehydrated lyophilised microsphere — 109

FIG. 9

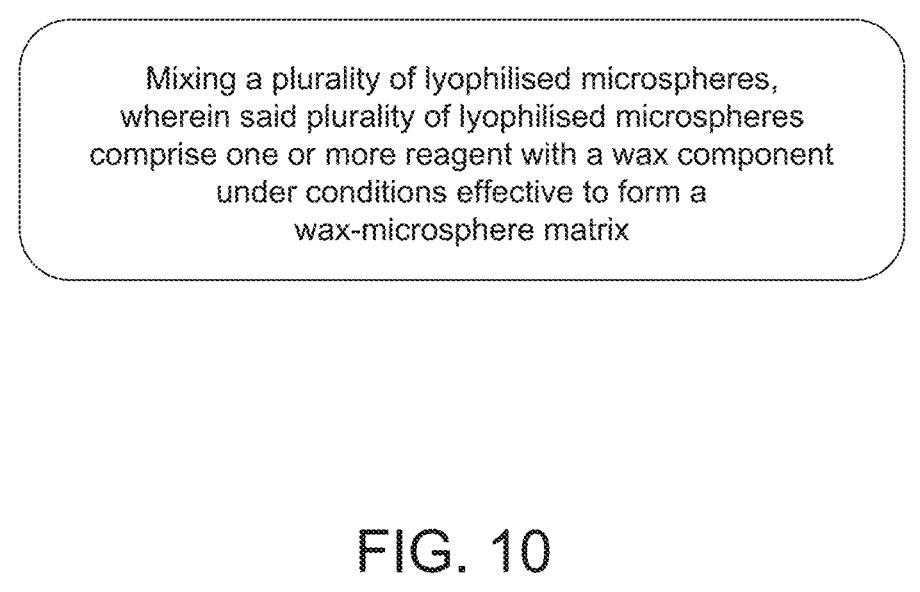

Mixing a plurality of lyophilised microspheres,
wherein said plurality of lyophilised microspheres
comprise one or more reagent with a wax component
under conditions effective to form a
wax-microsphere matrix

FIG. 10

Wax-encapsulated Mg

Wax
(~44 µL)

4 mm

Mg µSpheres
(~29)

WAX-MICROSPHERE MATRIX COMPOSITIONS AND METHODS OF MAKING AND USING THE SAME

FIELD

The present disclosure relates generally to wax-microsphere matrix compositions and methods of making and using the same.

BACKGROUND

Many current sequencing platforms use "sequencing by synthesis" ("SBS") technology and fluorescence-based methods for detection. Alternative sequencing methods and improved sample and library preparation processes that allow for more cost effective, rapid, and convenient sequencing and nucleic acid detection are desirable as complements to SBS.

Current protocols for SBS technology routinely employ a sample preparation process that converts DNA or RNA into a library of fragmented templates suitable for sequencing. Sample preparation methods often involve multiple steps, material transfers, and expensive instruments to effect fragmentation, and, therefore, are often difficult, tedious, expensive, and inefficient.

Libraries including polynucleotides are generally prepared in any suitable manner to attach oligonucleotide adapters to target polynucleotides. Sequencing may result in determination of the sequence of the whole, or a part of the target polynucleotides. The number of steps involved to transform nucleic acids into adapter-modified templates in solution ready for cluster formation and sequencing can be reduced, or in some instances even minimized, by the use of transposase mediated fragmentation and tagging. This process, referred to as "tagmentation," involves the modification of nucleic acids by a transposome complex comprising transposase enzyme complexed with adapters comprising transposon end sequence, as described in, for example, WO 2016/130704. Methods for immobilizing and amplifying prior to sequencing are described in, for instance, U.S. Pat. No. 8,053,192. A library of templates may be used to prepare clustered arrays of nucleic acid colonies, as described in U.S. Pat. Publ. No. 2005/0100900, by solid-phase amplification and more particularly solid phase isothermal amplification.

Sequencing can be carried out using any suitable sequencing technique, and methods for determining the sequence of immobilized and amplified adapter-target-adapter molecules, including strand re-synthesis, are known in the art and are described in, for instance, U.S. Pat. No. 8,053,192. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. Exemplary SBS systems and methods are described in U.S. Pat. Publ. No. 2007/0166705.

There are various problems that block efficiency of sample preparation compositions and processes for sequencing. For example, there are difficulties in staggering dissolution of multiple reagents within a common well. There are problems of differentiating between different reagents in terms of dissolving time. There are also problems of purifying atmospheric-captured water for sample and library preparation compositions and processes for sequencing. There are problems handling microspheres in a cartridge, in particular, due to the tendency of microspheres to electrostatically cling to surfaces including the sides and top of a well.

Accordingly, there is a need for improved sample preparation compositions and processes. In particular, there is a need for sequencing reagents, sample preparation reagents, sample extraction reagents, enrichment reagents, clustering reagents, and library preparation reagents with improved stability and associated compositions, methods, cartridges, and systems that demonstrate improved efficiency of workflow and tagmented library production and, in turn, increased read enrichment for the resulting libraries and simplified workflows.

The present disclosure is directed to overcoming these and other deficiencies in the art.

SUMMARY

A first aspect relates to a method. The method includes exposing a composition comprising a wax-microsphere matrix to a first melt-condition, wherein said wax-microsphere matrix comprises a wax component and a plurality of lyophilised microspheres, wherein said plurality of lyophilised microspheres comprise one or more reagent, whereby exposing said composition comprising said wax-microsphere matrix to said first melt-condition melts the wax component; exposing said composition to a first release-condition to rehydrate at least one lyophilised microsphere; and exposing said at least one rehydrated lyophilised microsphere to a separation-condition to separate said wax component from said at least one rehydrated lyophilised microsphere.

In one implementation, the first melt-condition comprises a modification of temperature. In one implementation, the first melt-condition comprises a temperature of above about 40° C.

In one implementation, the method further includes exposing the composition to a second melt-condition to melt the wax component, wherein the second melt-condition is different from the first melt-condition. In another implementation, the first release-condition comprises addition of an aqueous solution. In one implementation, the first release-condition comprises mixing the composition and the aqueous solution.

In one implementation, at least one of the plurality of lyophilised microspheres comprise a shell surrounding an interior compartment, wherein the interior compartment comprises the one or more reagent.

In one implementation, the method further includes exposing the composition to a second release-condition. In one implementation, the second release-condition releases the one or more reagent. In one implementation, the second release-condition is different from the first release-condition. In another implementation, the method further includes exposing the composition to a third release-condition to release at least one reagent, wherein the third release-condition is different from the first release condition and the second release condition.

In one implementation, the separation-condition comprises a modification of temperature. In another implementation, the separation-condition comprises a temperature at or below about 40° C. In another implementation, the method further includes removing the wax component after the separation-condition.

In one implementation, the one or more reagent comprises a sample preparation reagent, a sample extraction reagent, a library preparation reagent, an enrichment reagent, a clustering reagent, a sequencing reagent, or any combination thereof. In one implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof.

In one implementation the method further includes using the at least one rehydrated lyophilised microsphere in a sequencing by synthesis process. In another implementation, the method further includes using the at least one rehydrated lyophilised microsphere in a library preparation process. In yet another implementation, the method further includes using the at least one rehydrated lyophilised microsphere in a sample preparation process.

In one implementation, the plurality of lyophilised microspheres comprise one or more dry reagent, one or more bead, one or more powder, one or more cake, or any combination thereof. In one implementation, the second release-condition releases one or more reagent. In one implementation, the third release-condition releases one or more reagent. In one implementation, where the one or more reagent comprises a plurality of reagents, the plurality of reagents contain at least two different reagents. In one implementation, where the one or more reagent comprises a plurality of reagents, the plurality of reagents contain at least one reagent which is identical to at least one other reagent. In one implementation, the plurality of microspheres comprise more than one reagent. In one implementation, the plurality of microspheres comprise one reagent. In one implementation, exposing the composition to the first melt-condition, the first release-condition, and the separation-condition occurs sequentially or in order.

In one implementation, the wax component comprises a wax selected from spermaceti, Japan wax, paraffin, ceresin, ozocerite, bees wax, candelilla, montan, barnsdahl, ouricury, carnauba, or any combination thereof.

In an implementation, the method further includes flowing the one or more reagent of the at least one rehydrated lyophilised microsphere through a flow cell. In another implementation, the method further includes flowing the one or more reagent of the at least one rehydrated lyophilised microsphere through a flow cell during a sequencing by synthesis process.

A second aspect relates to a method of preparing a wax-microsphere matrix. The method includes mixing a plurality of lyophilised microspheres, wherein said plurality of lyophilised microspheres comprise one or more reagent, with a wax component under conditions effective to form a wax-microsphere matrix.

In one implementation, the wax-microsphere matrix comprises a random distribution of the plurality of lyophilised microspheres. In one implementation, the wax-microsphere matrix comprises a uniform distribution of the plurality of lyophilised microspheres. In one implementation, the wax-microsphere matrix is at a temperature of above about 40° C. In one implementation, the method further includes lowering the temperature of the wax-microsphere matrix under conditions effective to solidify the wax component. In one implementation, lowering the temperature of the wax-microsphere matrix comprises a temperature of at or below about 40° C.

In one implementation, at least one of the plurality of lyophilised microspheres comprise a shell surrounding an interior compartment, wherein the interior compartment comprises the one or more reagent. In one implementation, the one or more reagent comprises a sample preparation reagent, a sample extraction reagent, a library preparation reagent, an enrichment reagent, a clustering reagent, a sequencing reagent, or any combination thereof. In one implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In another implementation, the plurality of lyophilised microspheres comprise one or more dry reagent, one or more bead, one or more powder, one or more cake, or any combination thereof. In one implementation, where the one or more reagent comprises a plurality of reagents, the plurality of reagents contain at least two different reagents. In one implementation, where the one or more reagent comprises a plurality of reagents, the plurality of reagents contain at least one reagent which is identical to at least one other reagent.

In one implementation, the wax component comprises a wax selected from spermaceti, Japan wax, paraffin, ceresin, ozocerite, bees wax, candelilla, montan, barnsdahl, ouricury, carnauba, or any combination thereof.

In an implementation, the method of preparing a wax-microsphere matrix further includes forming a wax component in a mold, the wax component including a cavity; and sealing the cavity with wax after the mixing. In another implementation, mixing comprises filling the cavity with the plurality of lyophilised microspheres. In yet another implementation, the volume of the wax component is about 40 μL to about 50 μL. In still another implementation the volume of the cavity is about 10 μL to about 80 μl.

A third aspect relates to a composition. The composition includes a wax-microsphere matrix, said wax-microsphere matrix comprising: a wax component and a plurality of lyophilised microspheres, wherein said plurality of lyophilised microspheres comprise one or more reagent.

In one implementation, at least one of the plurality of lyophilised microspheres comprise a shell surrounding an interior compartment, wherein the interior compartment comprises the one or more reagent. In one implementation, the one or more reagent comprises a sample preparation reagent, a sample extraction reagent, a library preparation reagent, an enrichment reagent, a clustering reagent, a sequencing reagent, or any combination thereof. In one implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In one implementation, when the one or more reagent comprises a plurality of reagents, the plurality of reagents contain at least two different reagents. In one implementation, when the one or more reagent comprises a plurality of reagents, the plurality of reagents contain at least one reagent which is identical to at least one other reagent.

In one implementation, the wax component comprises a wax selected from spermaceti, Japan wax, paraffin, ceresin, ozocerite, bees wax, candelilla, montan, barnsdahl, ouricury, carnauba, or any combination thereof.

A fourth aspect relates to a method. The method includes elevating a temperature of a composition comprising a wax-microsphere matrix in a well from a first temperature to a second temperature; flowing a liquid in said well; mixing said composition and said liquid in said well; and lowering the temperature of said liquid from the second temperature to a third temperature under conditions effective to release one or more reagent from said wax-microsphere matrix.

In one implementation, the wax-microsphere matrix includes a wax component and a plurality of lyophilised microspheres, wherein the plurality of lyophilised microspheres comprise the one or more reagent. In one implementation, the second temperature is above about 40° C. In one implementation, the third temperature is at or below about 40° C. In one implementation, the second temperature releases at least one reagent. In one implementation, the mixing further comprises addition of an aqueous solution in the well. In one implementation, the mixing comprises mixing the composition and the aqueous solution.

In one implementation, the wax-microsphere matrix comprises a plurality of lyophilised microspheres and at least one of the plurality of lyophilised microspheres comprises a shell surrounding an interior compartment, wherein the interior compartment comprises the one or more reagent. In one implementation, the second temperature releases the interior compartment. In one implementation, the method further includes exposing the composition to one or more additional temperature modifications. In one implementation, the one or more temperature modifications release at least one reagent. In one implementation, the one or more additional temperature modifications are to a temperature that is different from the second temperature.

In one implementation, the method further includes exposing the composition to one or more additional temperature modifications to release at least one reagent, wherein the one or more additional temperature modifications are to a temperature that is different from the third temperature. In one implementation, the method further includes removing the wax component after releasing one or more reagent from the wax-microsphere matrix.

In one implementation, the one or more reagent comprises a sample preparation reagent, a sample extraction reagent, a library preparation reagent, an enrichment reagent, a clustering reagent, a sequencing reagent, or any combination thereof. In another implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In one implementation, the plurality of lyophilised microspheres comprise one or more dry reagent, one or more bead, one or more powder, one or more cake, or any combination thereof.

In one implementation, the first temperature is different from the third temperature. In one implementation, the first temperature is the same as the third temperature.

In one implementation, the method further includes flowing said one or more reagent through a flow cell. In one implementation, the method further includes flowing said one or more reagent through a flow cell during a sequencing by synthesis process.

A fifth aspect relates to a cartridge. The cartridge includes a reagent reservoir, the reagent reservoir comprising a wax-microsphere matrix composition, said wax-microsphere matrix composition comprising a wax component and a plurality of lyophilised microspheres, wherein said plurality of lyophilised microspheres comprise one or more reagent.

In one implementation, at least one of the plurality of lyophilised microspheres comprise a shell surrounding an interior compartment, wherein the interior compartment comprises the one or more reagent. In one implementation, the one or more reagent comprises a sample preparation reagent, a sample extraction reagent, a library preparation reagent, an enrichment reagent, a clustering reagent, a sequencing reagent, or any combination thereof. In one implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In one implementation, where the one or more reagent comprises a plurality of reagents, the plurality of reagents contain at least two different reagents. In one implementation, where the one or more reagent comprises a plurality of reagents, the plurality of reagents contain at least one reagent which is identical to at least one other reagent.

In one implementation, the wax component comprises a wax selected from spermaceti, Japan wax, paraffin, ceresin, ozocerite, bees wax, candelilla, montan, barnsdahl, ouricury, carnauba, or any combination thereof. In one implementation, the cartridge further includes a plurality of wax-microsphere matrix compositions in the reagent reservoir.

A sixth aspect relates to a system for controlling release of one or more reagent. The system includes a well; a wax-microsphere matrix composition, said wax-microsphere matrix composition comprising a wax component and a plurality of lyophilised microspheres, wherein said plurality of lyophilised microspheres comprise one or more reagent; and a liquid.

In one implementation, the liquid is in the well. In one implementation, the composition is in the well. In one implementation, the system further includes a temperature controller on the well.

Handling microspheres in a cartridge is proving to be a significant challenge. During the rehydration step, all sides and top of the wells need to be washed due to the tendency of microspheres to electrostatically cling to surfaces. To leverage the benefits of gravity, the lyophilised microspheres described herein are bulk encapsulated in a wax matrix as a slug (interchangeably referred to herein as "wax-microsphere matrix", "slug", and "wax slug") that can easily be handled and dropped into wells. Due to its weight, the position of the microspheres is predictable and can therefore easily be rehydrated in full.

Microspheres described herein are encapsulated in bulk in a wax slug that can easily be dispensed into wells. To release the microspheres and rehydrate them, the temperature is raised above the melting point of the wax and water is added to the solution. Wax then separates out of the liquid phase, and by dropping the temperature, can be isolated away from the rehydrate liquid reagent.

In accordance with the present disclosure, the methods, compositions, cartridges, and systems described herein have many advantages.

The various problems of handling microspheres within a common well or cartridge can be solved using the methods, compositions, cartridges, and systems as described herein.

BRIEF DESCRIPTION OF THE DRAWINGS

FIG. 1A shows current state microspheres which are scattered throughout the well by electrostatic cling. Thus, microspheres are located on sides and top of wells and the well needs washing of the sides and top. FIG. 1B shows improvement with use of wax slugs containing microspheres described herein.

FIG. 2A and FIG. 2B show a wax slug that contains microspheres and wax slug after placement on thermomixer at 1000 rpm to keep the microspheres in suspension and after temperature is dropped to 40° C. to solidify wax while mixing. FIG. 2C shows an extracted wax slug containing microspheres as described herein. Shown is the production of a wax slug containing microspheres in accordance with the present disclosure. Wax slugs may be prepared by dispensing dry microspheres into a well plate, dispensing wax in a liquid state (warm) or dry state (cold), shaking the well plate at a warm temperature, centrifuging the plate at a warm temperature, shaking plate at warm temperature, and setting plate at room temperature, followed by the dropping or flipping the plate to extract the slug.

FIG. 3 shows mixing of microspheres with wax in a large container, creating droplets that solidify as they gravitate down a cooling tower.

FIG. 5A shows a wax-microsphere matrix composition at about 20° C. FIG. 5B shows the wax-microsphere matrix at about 70° C. FIG. 5C shows the wax-microsphere matrix composition at about 70° C. after water is added, with wax being found at the top of the composition and microspheres being rehydrated. FIG. 5D shows the wax-microsphere matrix composition after rehydration and at about 20° C. with the wax being located at the top of the composition. FIG. 5E shows the separation of the wax and reagent that is released upon rehydration of the microspheres from the wax-microsphere matrix composition.

FIG. 6A shows a wax-microsphere matrix composition described herein (e.g., a "slug" or "wax slug") inside a tube. FIG. 6B shows melting of the wax component of the wax-microsphere matrix composition. FIG. 6C shows addition of rehydration buffer to the melted wax component of the wax-microsphere matrix composition. FIG. 6D shows mixing of the melted wax component of the wax-microsphere matrix composition to rehydrate microspheres. FIG. 6E shows one example of moving the wax component, by pushing the solution up with air (or physically flipping the well). FIG. 6F shows solidification of the wax component. FIG. 6G shows pulling back of air to drop the reagent(s) (which may alternatively be achieved by physically flipping the well).

FIG. 9 shows a flow chart describing one aspect described herein for a method.

FIG. 10 shows a flow chart describing one aspect described herein for a method of preparing a wax-microsphere matrix.

Figure 1A:
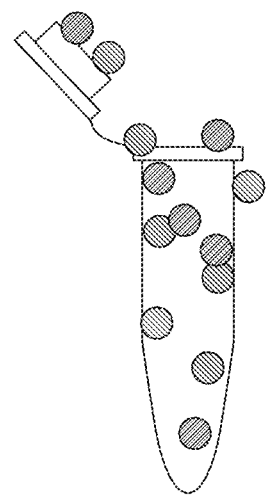
FIG. 1A and FIG. 1B show improvement and mitigation of existing microsphere usage with wax slugs containing microspheres as described herein.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

DETAILED DESCRIPTION

A first aspect relates to a method. The method includes exposing a composition comprising a wax-microsphere matrix to a first melt-condition, wherein said wax-microsphere matrix comprises a wax component and a plurality of lyophilised microspheres, wherein said plurality of lyophilised microspheres comprise one or more reagent, whereby exposing said composition comprising said wax-microsphere matrix to said first melt-condition melts the wax component; exposing said composition to a first release-condition to rehydrate at least one lyophilised microsphere; and exposing said at least one rehydrated lyophilised microsphere to a separation-condition to separate said wax component from said at least one rehydrated lyophilised microsphere.

It is to be appreciated that certain aspects, modes, implementations, variations, and features of the present disclosure are described below in various levels of detail in order to provide a substantial understanding of the present technology. Unless otherwise noted, all technical and scientific terms used herein generally have the same meaning as commonly understood by one of ordinary skill in the art. The use of the term "including" as well as other forms is not limiting. The use of the term "having" as well as other forms is not limiting. As used in this disclosure, whether in a transitional phrase or in the body of the claim, the terms "comprise(s)" and "comprising" are to be interpreted as having an open-ended meaning. That is, the terms are to be interpreted synonymously with the phrases "having at least" or "including at least."

The terms "substantially", "approximately", "about", "relatively", or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, fluctuations can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It is further appreciated that certain features described herein, which are, for clarity, described in the context of separate implementations, can also be provided in combination in a single implementation. Conversely, various features which are, for brevity, described in the context of a single implementation, can also be provided separately or in any suitable sub-combination.

The terms "connect", "contact", and/or "coupled" include a variety of arrangements and assemblies. These arrangements and techniques include, but are not limited to, (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (optionally with the presence of one or more additional components therebetween). Components that are in direct physical contact with one another may or may not be in electrical contact and/or fluid contact with one another. Moreover, two components that are electrically connected, electrically coupled, optically connected, optically coupled, fluidly connected, or fluidly coupled may or may not be in direct physical contact, and one or more other components may be positioned between those two connected components.

As described herein, the term "attached" may include when two things are joined, fastened, adhered, connected, or bound to one another. A reaction component, like a polymerase, can be attached to a solid phase component, like a conductive channel, by a covalent or a non-covalent bond. As described herein, the phrase "covalently attached" or "covalently bonded" refers to forming one or more chemical bonds that are characterized by the sharing of pairs of electrons between atoms. A non-covalent bond is one that does not involve the sharing of pairs of electrons and may include, for example, hydrogen bonds, ionic bonds, van der Waals forces, hydrophilic interactions, and hydrophobic interactions.

As described herein, the terms "polynucleotide" or "nucleic acids" refer to deoxyribonucleic acid (DNA), ribonucleic acid (RNA), or analogs of either DNA or RNA made from nucleotide analogs. The terms as used herein also encompasses cDNA, that is complementary, or copy DNA produced from an RNA template, for example by the action of reverse transcriptase. In one implementation, the nucleic acid to be analyzed, for example by sequencing through use of the described systems, is immobilized on a substrate (e.g., a substrate within a flow cell or one or more beads upon a substrate such as a flow cell, etc.). The term immobilized as used herein is intended to encompass direct or indirect, covalent, or non-covalent attachment, unless indicated otherwise, either explicitly or by context. The analytes (e.g., nucleic acids) may remain immobilized or attached to the support under conditions in which it is intended to use the support, such as in applications requiring nucleic acid sequencing. In one implementation, the template polynucleotide is one of a plurality of template polynucleotides attached to a substrate. In one implementation, the plurality of template polynucleotides attached to the substrate include a cluster of copies of a library polynucleotide as described herein.

Nucleic acids include naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g., found in deoxyribonucleic acid (DNA)) or a ribose sugar (e.g., found in ribonucleic acid (RNA)).

In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose may be bonded to N-1 of a pyrimidine or N-9 of a purine.

A nucleic acid can contain any of a variety of analogs of these sugar moieties that are known in the art. A nucleic acid can include native or non-native bases. A native deoxyribonucleic acid can have one or more bases selected from the group consisting of adenine, thymine, cytosine, or guanine and a ribonucleic acid can have one or more bases selected from the group consisting of uracil, adenine, cytosine or guanine. Useful non-native bases that can be included in a nucleic acid are known in the art.

The term nucleotide as described herein may include natural nucleotides, analogs thereof, ribonucleotides, deoxyribonucleotides, dideoxyribonucleotides and other molecules known as nucleotides. As described herein, a nucleotide may include a nitrogen containing heterocyclic base, a sugar, and one or more phosphate groups. Nucleotides may be monomeric units of a nucleic acid sequence, for example to identify a subunit present in a DNA or RNA strand. A nucleotide may also include a molecule that is not necessarily present in a polymer, for example, a molecule that is capable of being incorporated into a polynucleotide in a template dependent manner by a polymerase. A nucleotide may include a nucleoside unit having, for example, 0, 1, 2, 3 or more phosphates on the 5' carbon. Tetraphosphate nucleotides, pentaphosphate nucleotides, and hexaphosphate nucleotides may be useful, as may be nucleotides with more than 6 phosphates, such as 7, 8, 9, 10, or more phosphates, on the 5' carbon. Examples of naturally occurring nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include nucleotide analogs, such as those that are not present in a natural biological system or not substantially incorporated into polynucleotides by a polymerase in its natural milieu, for example, in a non-recombinant cell that expresses the polymerase. Non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different, or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties are described, for example, in U.S. Pat. No. 7,427,673, which is hereby incorporated by reference in its entirety. It will be understood that in some implementations a nucleotide analog having a 3' terminator moiety or lacking a 3' hydroxyl (such as a dideoxynucleotide analog) can be used under conditions where the polynucleotide that has incorporated the nucleotide analog is not further extended. In some implementations, nucleotide(s) may not include a reversible terminator moiety, or the nucleotides(s) will not include a non-reversible terminator moiety or the nucleotide(s) will not include any terminator moiety at all. In one implementation, the 3'-hydroxy blocking group is a reversible blocking group.

The term "cluster" refers to a discrete site on a solid support comprised of a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

As used herein, the term "different," when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other.

As used herein, a "library" is a population of polynucleotides from a given source or sample. A library comprises a plurality of target polynucleotides.

A modified nucleotide as described herein includes one that has a purine or pyrimidine base and a sugar moiety having a 3'-hydroxy blocking group. In one implementation, the modified nucleotide is linked to a detectable label. In one implementation, the detectable label comprises a fluorophore. This disclosure encompasses nucleotides including a fluorescent label (or any other detection tag) that may be used in any method disclosed herein, on its own or incorporated into or associated with a larger molecular structure or conjugate. Additional examples of detectable labels are described in U.S. Pat. No. 7,541,444, which is hereby incorporated by reference in its entirety.

The fluorescent label can include compounds selected from any known fluorescent species, for example rhodamines or cyanines. A fluorescent label as disclosed herein may be attached to any position on a nucleotide base, and may optionally include a linker. In one implementation, the modified nucleotide is linked to a detectable label via a cleavable linker. The function of the linker is generally to aid chemical attachment of the fluorescent label to the nucleotide. In particular implementations, Watson-Crick base pairing can still be carried out for the resulting analogue. A linker group may be used to covalently attach a dye to the nucleoside or nucleotide. A linker moiety may be of sufficient length to connect a nucleotide to a compound such that the compound does not significantly interfere with the overall binding and recognition of the nucleotide by a nucleic acid replication enzyme. Thus, the linker can also include a spacer unit. The spacer distances, for example, the nucleotide base from a cleavage site or label.

The linker may be cleavable and the cleavage site may be located at a position on the linker that results in part of the linker remaining attached to the nucleotide base after cleavage or that results in the whole linker being removed from the nucleotide base. Exemplary linkers include azide- and allyl-containing cleavable moieties, disulfide linkers, acid labile moieties (including dialkoxybenzyl moieties, Sieber linkers, indole moieties, t-butyl Sieber moieties), electrophilically cleavable moieties, nucleophilically cleavable moieties, photocleavable moieties, cleavage under reductive conditions, oxidative conditions, cleavage via use of safety-catch moieties, and cleavage by elimination mechanisms. Examples of such moieties are described in WO03/048387, which is hereby incorporated by reference in its entirety.

The composition may include different modified nucleotides linked to different detectable labels. In some implementations, four different modified nucleotides may be linked to four different detectable labels. Alternatively, four different modified nucleotides may be labeled with two different detectable labels (for example, for two-channel sequencing by synthesis) or with a single detectable label (for example, for one-channel sequencing by synthesis).

As used herein, a "nucleoside" is structurally similar to a nucleotide, but is missing the phosphate moieties. An example of a nucleoside analogue is one in which the label is linked to the base and there is no phosphate group attached to the sugar molecule. The term "nucleoside" is used herein in its ordinary sense as understood by those skilled in the art. Examples include, but are not limited to, a ribonucleoside including a ribose moiety and a deoxyribonucleoside including a deoxyribose moiety. A modified pentose moiety is a pentose moiety in which an oxygen atom is replaced with a carbon and/or a carbon is replaced with a sulfur or an oxygen atom. A "nucleoside" is a monomer that may have a substituted base and/or sugar moiety.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

The term substrate (or solid support), as described herein, may include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. For example, a substrate may be a glass surface (e.g., a planar surface of a flow cell channel). In one implementation, a substrate may include an inert substrate or matrix which is "functionalized," such as by applying a layer or coating of an intermediate material including reactive groups which permit covalent attachment to molecules such as polynucleotides. Supports may include polyacrylamide hydrogel supported on an inert substrate such as glass. Molecules (e.g., polynucleotides) may be directly covalently attached to an intermediate material (e.g., a hydrogel). A support may include a plurality of particles or beads each having a different attached analyte.

As used herein, "derivative" or "analogue" means a synthetic nucleotide or nucleoside derivative having modified base moieties and/or modified sugar moieties. Such derivatives and analogs are discussed in, for example, Bucher, N. "Nucleotide Analogs. Synthesis and Biological Function," *Angewandie Chemie* 97:564 (1980), which is hereby incorporated by reference in its entirety. Nucleotide analogs may also include modified phosphodiester linkages, including phosphorothioate, phosphorodithioate, alkylphosphonate, phosphoranilidate and phosphoramidate linkages. "Derivative", "analog", and "modified" as used herein, may be used interchangeably, and are encompassed by the terms "nucleotide" and "nucleoside" as described herein.

As used herein, the terms "solid phase" or "surface" are used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

As used herein, "substantially free of" a material (including, for example, a crowding agent or a nucleic acid) refers to compositions having less than 10% of the material, less than 5% of the material, less than 4% of the material, less than 3% of the material, less than 2% of the material, or less than 1% of the material.

The composition comprising a wax-microsphere matrix as described herein includes a wax component and a plurality of lyophilised microspheres, where the plurality of lyophilised microspheres include one or more reagent.

The wax component as described herein may include any suitable amount of wax, wax ingredient, or wax compound that is suitable for melting when exposed to one or more melt conditions, and thereby expose the wax-microsphere matrix composition to a first release-condition to rehydrate at least one lyophilised microsphere. The wax component may include, but is not limited to, spermaceti, Japan wax, paraffin, ceresin, ozocerite, bees wax, candelilla, montan, barnsdahl, ouricury, carnauba, or any combination thereof. Examples of types of wax that may be useful and their respective melting points are provided in Table 1.

TABLE 1

| Wax Types and Melting Points. | |
| --- | --- |
| Wax | Melting Point (° C.) |
| Spermaceti | 41-49 |
| Japan Wax | 53 |
| Paraffin | 53-55 |
| Ceresin | 54-77 |
| Ozocerite | 58-100 |
| Bees Wax | 61-63 |
| Candelilla | 65-70 |
| Montan | 76-84 |
| Barnsdahl | 70-74 |
| Ouricury | 79-84 |
| Carnauba | 80-87 |

As used herein, "microsphere" includes spherical particles or beads that have a diameter or cross-section of 0.1 μm to 25,000 μm. For example, a microsphere may have a diameter of about 0.1 μm, 0.5 μm, 1 μm, 10 μm, 20 μm, 25 μm, 30 μm, 35 μm, 40 μm, 50 μm, 60 μm, 70 μm, 80 μm, 90 μm, 100 μm, 150 μm, 200 μm, 300 μm, 400 μm, 500 μm, 600 μm, 700 μm, 800 μm, 900 μm, 1,000 μm, 10,000 μm, 25,000 μm, or any diameter between about 0.1 μm and about 25,000 μm. In one implementation, the microsphere has a diameter between about 100 μm and about 1,000 μm. In one implementation, the microsphere has a cross-section of between about 0.1 mm and about 25 mm. In one implementation, the microsphere has a cross-section of between about 0.1 mm and about 1 mm. In one implementation, the microsphere has a cross-section of greater than about 1 mm. In one implementation, the microsphere has a diameter of about 0.1 mm, 1 mm, 2 mm, 3 mm, 4 mm, 5 mm, 6 mm, 7 mm, 8 mm, 9 mm, 10 mm, 50 mm, 100 mm, 200 mm, 300 mm, 400 mm 500 mm, 600 mm, 700 mm, 800 mm, 900 mm, 1,000 mm, or any diameter between about 0.1 mm and about 1,000 mm.

A lyophilised microsphere as described herein includes any compound that comprises lyophilised reagents. In one implementation, the microsphere is spherical, elliptical, or toroidal. Microspheres are generally comprised of an outer polymer layer and may include one or more of the ingredients described herein. Microspheres may include, for example, biodegradable polymers. Microspheres in accordance with the present disclosure include those prepared by conventional techniques, which are known to those skilled in the art. For example, microspheres may be prepared by freezing a liquid into frozen pellets, followed by placing frozen microspheres in a dryer, for example, dried by heat or in tray lyophilisers such as a conventional tray dryer, or in a rotational dryer. In the present disclosure, the term "lyophilize" or "lyophilizate" will be used as equivalent terms of "lyophilised", "lyophilizate", or "freeze-dried" e.g., with respect to a compositions, methods, cartridges, and systems described herein. Microencapsulation as described herein includes the coating of individual microspheres or particles in one or more powder.

Macrospheres in accordance with the present disclosure include those prepared by conventional techniques, which are known to those skilled in the art. The compositions, methods, cartridges, and systems described herein may include a single microsphere, or may include a plurality of microspheres and may thereby form a macrosphere. For example, the composition described herein may include anywhere between 1 and over 1,000,000 microspheres. In one implementation, the composition includes 1 microsphere, or less than 25 microspheres, or less than 50 microspheres, or less than 75 microspheres, or less than 100 microspheres, or less than 500 microspheres, or any number of microspheres between about 1 and about 1,000,000. In one implementation, for example in a macrosphere, compositions and/or reagents are different. Macroencapsulation as described herein includes the coating of a plurality of microspheres or particles in one or more powder.

The lyophilised microspheres may include a shell surrounding an interior compartment, wherein the interior compartment comprises the one or more reagent.

As described herein, a "shell" includes a composition that surrounds an interior compartment. The interior compartment as described herein includes the one or more reagent. As described herein, the method may include exposing the composition to a second release condition. The second release-condition may, in one implementation, release the one or more reagent. The shell in the composition may release the interior compartment when the shell is exposed to a second release-condition. The interior compartment of the composition described herein may release one or more reagent when the interior compartment is exposed to a second release condition. The interior compartment may, for example, have its own interior compartment shell that surrounds the one or more reagent. The first release condition may be different from the second release condition.

As described herein, the first release-condition is suitable to rehydrate at least one lyophilised microspheres. As further described herein, the second release-condition is suitable to release at least one reagent. Rehydration of the at least one lyophilised microsphere as described herein does not necessarily require release of one or more reagent. Release of one or more reagent as described herein depends on the rehydration of the at least one lyophilised microsphere as described herein.

As described herein, "encapsulate", "encapsulated", and "encapsulation" may include the enclosing of one or more compositions as described herein. Microencapsulation as described herein refers to the embedding of at least one ingredient, for example, an active agent, into at least one other material, for example, a shell material. Encapsulation in accordance with the present disclosure includes, but is not limited to, bulk encapsulation, matrix encapsulation, macroencapsulation, microencapsulation, nano encapsulation, single molecule, and ionic encapsulation.

In one implementation, the interior compartment includes a plurality of microspheres comprising a plurality of reagents. In another implementation, the interior compartment includes a plurality of microspheres comprising one reagent. As described herein, each of the plurality of microspheres may include a plurality of reagents. Alternatively, the plurality of microspheres may collectively include a plurality of reagents.

Lyophilisable formulations can be reconstituted into solutions, suspensions, emulsions, or any other suitable form for administration or use. Lyophilisable formulations are typically first prepared as liquids, then frozen and lyophilised. The total liquid volume before lyophilisation can be less than, equal to, or more than, the final reconstituted volume of the lyophilised formulation. The final reconstituted volume of the lyophilised formulation may be less than the total liquid volume before lyophilisation, or may be greater than the total liquid volume before lyophilisation, or may be an equivalent total liquid volume to before lyophilisation.

Lyophilised formulations can be stored at a wide range of temperatures. Lyophilised formulations may be stored below 25° C., for example, refrigerated at 2-8° C., or at room temperature (e.g., approximately 25° C.). Lyophilised formulations may be stored at about 0° C., 5° C., 10° C., 15° C., 20° C., 25° C., 30° C., 35° C., 37° C., or any temperature between 37° C. and –80° C. For example, they compositions may be stored between about 15° C. and about 37° C., below about 25° C., between about 4-20° C.; below about 4° C.; below about –20° C.; about –40° C.; about –70° C., or about –80° C. Stability of the lyophilised formulation may be determined in a number of ways known in the art, for example, by visual appearance of the composition and/or by moisture content. The wax-microsphere matrix compositions of the present disclosure can withstand temperature excursions that might occur during shipping, for example, up to 70° C. The compositions, methods, cartridges, and systems described herein, in one implementation, exhibit stability when stored for a period of time, for example, 10 days, 14 days, 20 days, 26 days, 30 days, 60 days, 100 days, 200 days, 300 days, 365 days, or more, when stored at a temperature of 37° C. for example.

Lyophilised formulations are typically rehydrated (interchangeably referred to herein as "reconstituted") for use by addition of an aqueous solution to dissolve the lyophilised formulation. A wide variety of aqueous solutions can be used to reconstitute a lyophilised formulation including water, saline, or another electrolyte or non-electrolyte diluent. It may be preferable in certain circumstances that the lyophilised compositions described herein are reconstituted using water. Lyophilised formulations may be rehydrated with a solution comprising water (e.g., USP WFI, or water for injection) or bacteriostatic water (e.g., USP WFI with 0.9% benzyl alcohol). However, solutions comprising additives, buffers, excipients, and/or carriers can also be used.

The first release-condition may further include addition of an aqueous solution. The aqueous solution may include any aqueous solution suitable for rehydration of a lyophilised microsphere. The first release-condition may, in one implementation, include mixing the composition and the aqueous solution.

Freeze-dried or lyophilised formulations are typically prepared from liquids, that is, from solutions, suspensions, emulsions, and the like. Thus, the liquid that is to undergo freeze-drying or lyophilisation may include all components desired in a final reconstituted liquid formulation. Alternatively, the liquid that is to be lyophilised may include a single reagent, then, once lyophilised, be dry compounded together with one or more additional lyophilised reagents such that those reagents are mixed together upon rehydration to form the reconstituted liquid formulation. Accordingly, one lyophilised material may be rehydrated, or, two or more lyophilised materials may be rehydrated together. As a result, when rehydrated or reconstituted, the freeze-dried or lyophilised formulation will render a desired liquid formulation upon reconstitution.

In one implementation, the wax-microsphere matrix composition described herein, when lyophilised, includes a moisture content of below about 10 wt. %. For example, the moisture content may be less than about 9.5 wt. %, less than about 9 wt. %, less than about 8.5 wt. %, less than about 8 wt. %, less than about 7.5 wt. %, less than about 7 wt. %, less than about 6.5 wt. %, less than about 6 wt. %, less than about 5.5 wt. %, less than about 5 wt. % water, less than about 4.5 wt. %, less than about 4 wt. %, less than about 3.5 wt. %, less than about 3 wt. %, less than about 2.5 wt. %, less than about 2 wt. %, less than about 1.5 wt. %, less than about 1 wt. %, less than about 0.5 wt. %, less than about 0.1 wt. % water, or any amount therebetween. In one implementation, there is no measurable content of water in the wax-microsphere matrix composition.

The method described herein includes exposing the wax-microsphere matrix composition that includes a wax-microsphere matrix to a first melt-condition. The first melt-condition includes any condition suitable to melt the wax component. In one implementation, the first melt-condition includes a modification of temperature. The modification of temperature provided by the first melt-condition includes a temperature of, for example, above about 40° C. The temperature in the first melt-condition may be, for example, between about 40° C. and about 41° C., about 41° C., about 42° C., about 43° C., about 44° C., about 45° C., about 50° C., about 55° C., about 60° C., about 65° C., about 70° C., about 75° C., about 80° C., about 85° C., about 90° C., about 95° C., about 100° C., above about 100° C., or any temperature suitable to achieve melt of the wax component.

The method, in one implementation, may further include exposing the composition to a second melt-condition to melt the wax component, where the second melt-condition is different from the first melt-condition. The second melt condition may likewise be above about 40° C. For example, the second melt-condition may be between about 40° C. and about 41° C., about 41° C., about 42° C., about 43° C., about 44° C., about 45° C., about 50° C., about 55° C., about 60° C., about 65° C., about 70° C., about 75° C., about 80° C., about 85° C., about 90° C., about 95° C., about 100° C., above about 100° C., or any temperature suitable to achieve melt of the wax component.

The method described herein further includes exposing the composition to a first release-condition. The first release-condition includes any condition suitable to rehydrate at least one lyophilised microsphere. The first release-condition described herein may, in one implementation, release at least one reagent. In another implementation, the second release-condition releases one or more reagent. In yet another implementation, the third release-condition releases one or more reagent. Accordingly, the first release-condition, the second release-condition, and the third release-condition may all or individually release one or more reagent. The first release-condition, the second release-condition, and the third release-condition may operate independently of one another. In one implementation, when the one or more reagent comprises a plurality of reagents, the plurality of reagents contain at least two different reagents. In another implementation, when the one or more reagent comprises a plurality of reagents, the plurality of reagents contain at least one reagent which is identical to at least one other reagent. In yet another implementation, the plurality of microspheres may include more than one reagent (e.g., two or more types of reagents). Alternatively, the plurality of microspheres may include one reagent (e.g., a single type of reagent).

As used herein, the term "reagent" describes a single agent or a mixture of two or more agents useful for reacting with, interacting with, diluting, or adding to a sample, and may include the compositions described herein as well as agents used in nucleic acid reactions, including, for example buffers, chemicals, enzymes, polymerase, primers including those having a size of less than 50 base pairs, template nucleic acids, nucleotides, labels, dyes, or nucleases.

In one implementation, the one or more reagent is a sample preparation reagent, a library preparation reagent, an enrichment reagent, a clustering reagent, a sequencing reagent, or a combination thereof. In one implementation, the one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In some implementations, the reagent may further or alternatively include a lysozyme, proteinase K, random hexamers, transposase (for example, Tn5), primers (for example, P5 and P7 adaptor sequences), ligase, catalyzing enzyme, deoxynucleotide triphosphates, buffers, or divalent cations. The reagent may further or alternatively include, for example, bead-linked transposomes (BLT), Tris pH7, $MgCl_2$, Mg acetate, Mg sulfate, indexed primers, Q5 polymerase, B st3.0, Tris pH9, dNTPs, NaCl, betaine, or any combination thereof. A reagent as described herein may, in certain implementations, include enzymes such as polymerases, ligases, recombinases, or transposases; binding partners such as antibodies, epitopes, streptavidin, avidin, biotin, lectins or carbohydrates; or other biochemically active molecules. Other examples reagents include reagents for a biochemical protocol, such as a nucleic acid amplification protocol, an affinity-based assay protocol, an enzymatic assay protocol, a sequencing protocol, and/or a protocol for analyses of biological fluids. According to some implementations disclosed herein, a reagent may include one or more beads, in particular magnetic beads, depending on specific workflows and/or downstream applications.

In one implementation, a reagent in accordance with the present disclosure is a polymerase. As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (Bacillus stearothermophilus) polymerase, exo-Klenow polymerase or sequencing grade T7 exo-polymerase. Some polymerases may degrade the strand in front of them, effectively replacing it with the growing chain behind (5' exonuclease activity). Some polymerases have an activity that may degrade the strand behind them (3' exonuclease activity). Some useful polymerases have been modified, either by mutation or otherwise, to reduce or eliminate 3' and/or 5' exonuclease activity.

Polymerase in accordance with the present disclosure may include any polymerase that can tolerate incorporation of a phosphate-labeled nucleotide. Examples of polymerases that may be useful in accordance with the present disclosure include but are not limited to phi29 polymerase, a klenow fragment, DNA polymerase I, DNA polymerase III, GA-1, PZA, phi15, Nf, G1, PZE, PRD1, B103, GA-1, 9oN polymerase, Bst, Bsu, T4, T5, T7, Taq, Vent, RT, pol beta, pol gamma, and combinations thereof. Polymerases engineered to have specific properties may be used. In one implementation, the polymerase may be useful for sequencing ("sequencing polymerase"). In one implementation, the reagent includes a polymerase, for example, Pol 812, 129 DNA polymerase, Taq polymerase, Bsu polymerase, or any combination thereof.

A primer as disclosed herein includes a nucleic acid molecule that can hybridize to a target sequence of interest. In several implementations, a primer may function as a substrate onto which nucleotides can be polymerized by a polymerase. However, in some examples, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In one implementation, the primer is a single-stranded oligonucleotide or polynucleotide.

Non-limiting examples of nucleic acid molecules that may be included in the compositions described above also include, DNA, such as genomic or cDNA; RNA, such as mRNA, sRNA or rRNA; or a hybrid of DNA and RNA. The composition may further comprise a labelled-nucleotide.

The term "salt" may include salts prepared from toxic or non-toxic acids or bases including inorganic acids and bases and organic acids and bases. Salts may be prepared from, for example, pharmaceutically acceptable non-toxic acids including inorganic and organic acids.

Any surfactant known to one skilled in the art may be also be included in the composition, particularly, when the composition is lyophilised. The surfactant may be polyionic, non-ionic, or ionic (specifically cationic or anionic), or may be zwitterionic. A surfactant as described herein includes Tween-20, Tween 80, CHAPS, or other detergent such as Brij-L23, Pluronic-F127, or a combination thereof. Examples of suitable surfactants include but are not limited to polyacrylate surfactants, silicone surfactants, and/or other commercially available surfactants or detergents. The composition described herein may include an anionic surfactant which contains an anionic functional group at one end, such as a sulfate, sulfonate, phosphate, and carboxylate functional group. The reagent may comprise a neutral surfactant, for example, a polyethelene glycol lauryl ether.

Sample preparation reagents as described herein may include, for example, lysis buffer, proteinase K (PK1), purification beads (PB), resuspension buffer (RSB), and ethanol (EtOH). Library preparation reagents as described herein may include, for example, end repair mix, A-Tailing mix, ligation mix, unique molecular identifiers (UMI), stop ligation buffer, as well as Tag buffers, nicotinamide-adenine dinucleotide ($NAD^+$), ligase, indexes, beads, SDS, switching oligos, dNTPs, and buffers.

The composition may further, or in the alternative, include an enzyme inhibitor, a molecular probe, a crowding agent, organic osmolite, cyclodextrin, adenosine triphosphate (ATP), ethylenediaminetetraacetic acid (EDTA), creatine kinase, creatine phosphate, palladium, lipoic acid, hexaethylene glycol, trihydroxypropanephosphine, sodium ascorbate, or any combination thereof. An enzyme inhibitor as described herein includes any a molecule that binds to an enzyme and decreases its activity. A molecular probe as described herein includes, for example, digoxigenin, 8-Anilinonaphthalene-1-sulfonic acid ("ANS"), porphyrin, BODIPY, cyanine, or any combination thereof. A crowding agent as described herein includes any crowding agent known to those skilled in the art. Examples include, but are not limited to, polyethylene glycol, ficoll, dextran, and serum albumin. In one implementation, the composition includes about 5 wt. %, about 4 wt. 5%, about 3 wt. 5, about 2 wt. %, about 1 wt. %, less than about 1 wt. % of a crowding agent, for example, less than about 0.001 wt. %, about 0.001 wt. %, about 0.005 wt. %, about 0.01 wt. %, about 0.05 wt. %, about 0.1 wt. %, about 0.5 wt. %, about 1 wt. % of an additional compound, or any amount or range therebetween. In one implementation, there is no measurable content of crowding agent in the composition.

Those skilled in the art of sequencing technologies will appreciate there are additional reagents that may be useful in the compositions, methods, kits, cartridges, and systems of the present disclosure that are not explicitly described herein.

The method described herein further includes exposing the rehydrated lyophilised microsphere to a separation-condition. The separation-condition includes any condition suitable to separate the wax component from the rehydrated lyophilised microsphere. In one implementation, the separation-condition comprises a modification of temperature. The modification of temperature provided by the separation-condition includes the wax-microsphere matrix having a temperature of, for example, at or below about 40° C. The temperature of the wax-microsphere matrix in the separation-condition may be, for example, between about 0° C. and about 40° C., about 39° C., about 38° C., about 37° C., about 36° C., about 35° C., about 34° C., about 33° C., about 32° C., about 31° C., about 30° C., about 25° C., about 24° C., about 23° C., about 22° C., about 21° C., about 20° C., about 19° C., about 18° C., about 17° C., about 16° C., about 15° C., about 10° C., about 5° C., about 4° C., about 3° C., about 2° C., about 1° C., about 0° C., or below about 0° C. The separation-condition may result in the wax component separating and moving to the top of the composition and/or well in which the composition is located. For example, the wax component may be separated by pushing the solution up with air or physically flipping the well.

In one implementation, the method further includes removing the wax component after the separation-condition. The wax component separates and the reagent is released upon rehydration of the microspheres released from the wax-microsphere matrix. Once the wax component is solidified, it may be removed from the composition and/or well in which the composition is located. For example, the solidified wax component may be removed by air that is pulled back or physically flipping the well. Alternatively, the solidified wax component may be moved from the composition and may remain in the well in which the composition is located.

In one implementation, exposing the composition to the first melt-condition, the first release-condition, and the separation-condition occurs sequentially or in order. For example, the composition may be exposed to the first melt-condition, then the first release-condition, then the separation-condition. Alternatively, the composition may be exposed to the first melt-condition, first release-condition, and separation-condition in any other order that is suitable for carrying out the methods described herein. The composition may, in one implementation, be exposed to the first melt-condition, first release-condition, and separation-condition simultaneously, or may be exposed to any two of the conditions simultaneously.

In accordance with the present disclosure, the compositions, methods, cartridges, and systems described herein have many advantages and benefits including, for example, increasing stability of reagents, use of macroencapsulation to enable multi-run cartridges, and use of a wax-microsphere matrix to enable simplified workflows, reduced number of reagent wells, and simplification of the manufacturing process (via, for example, static mitigation).

"Modifying" any of the conditions as described herein (e.g., by providing a first melt-condition, a first release-condition, a separation-condition) includes any change in one or more conditions in the composition and, or in the alternative, the environment surrounding the composition (e.g., a rehydration solution or other surrounding solution). Modifying the conditions in one implementation allows for melting of a wax component, release of one or more lyophilised microspheres, and/or release of any compound in the composition or release of one or more reagents in the interior compartment. One way to enable modification of conditions through temperature-triggered release. Other reaction characteristics may be modified in addition to or instead of time and, or in the alternative, temperature. For example, pH and humidity may be modified to further control release of one or more compounds, components, and reagent(s) contained therein. The conditions may be modified any number of times to produce any number of different conditions.

Figures 5A, 5B, 5C, 5D, 5E:
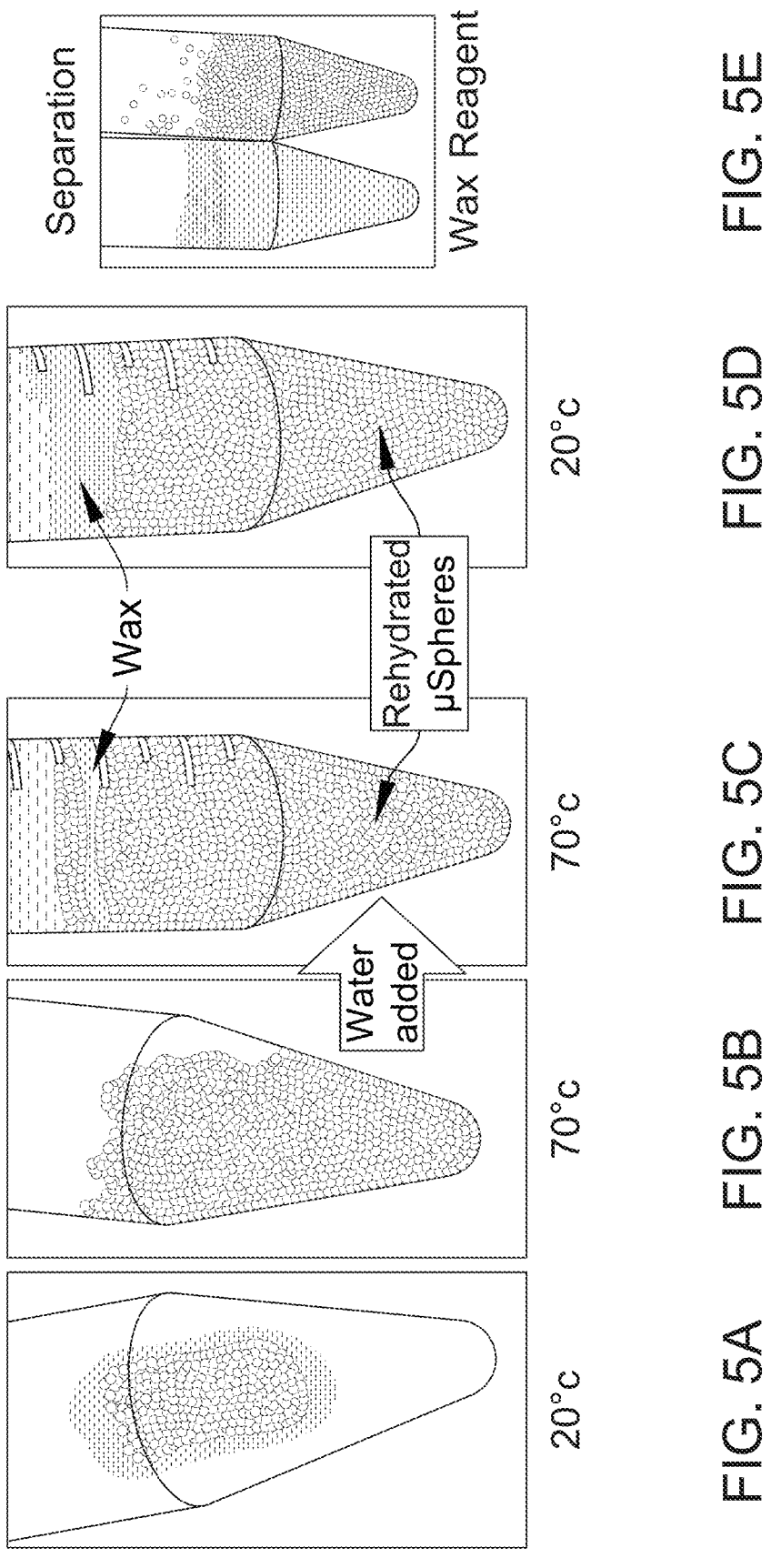
FIGS. 5A-5E show an example of a method of rehydration of the wax-microsphere matrix composition described herein.

In one implementation, as shown for example in FIGS. 5A-5E, the method of rehydration of the wax-microsphere composition may include the following steps: (1) a wax-microsphere matrix composition is provided at about 20° C. (FIG. 5A); (2) the temperature of the wax-microsphere matrix composition is elevated to about 70° C. (FIG. 5B); (3) water is added to the wax-microsphere matrix composition, and the wax component may be found at the top of the composition and the microspheres may be rehydrated (FIG. 5C); (4) the temperature of the wax-microsphere matrix composition is lowered to about 20° C., and the wax component may be located at the top of the composition (FIG. 5D); and (5) the wax component separates and the reagent is released upon rehydration of the microspheres from the wax-microsphere matrix composition.

Figures 6A, 6B, 6C, 6D, 6E, 6F, 6G:
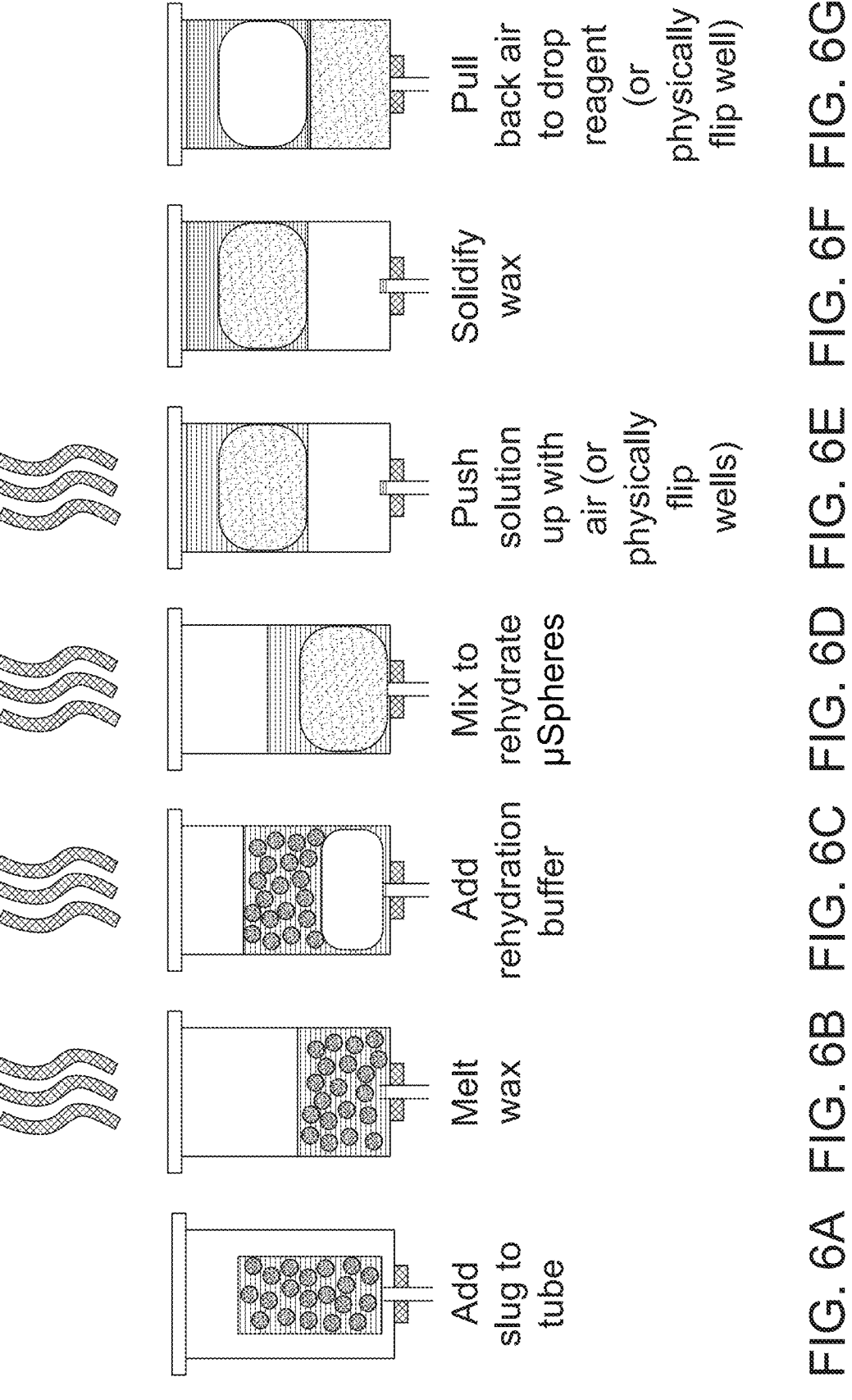
FIGS. 6A-6G show an example of a method of rehydration of the wax microsphere-matrix composition described herein.

In one implementation, as shown for example in FIGS. 6A-6G, the method of rehydration of the wax microsphere-matrix composition includes the following steps: (1) a wax-microsphere matrix composition is provided inside a tube or well (FIG. 6A); (2) the wax-microsphere matrix composition is exposed to a condition that melts to wax component (FIG. 6B); (3) a rehydration buffer is added to the wax-microsphere matrix composition having a melted wax component (FIG. 6C); (4) the wax-microsphere matrix composition having a melted wax component is mixed to rehydrate microspheres (FIG. 6D); (5) the wax component is moved to the top of the tube or well, for example, by pushing the solution up with air or physically flipping the well (FIG. 6E); (6) the wax component is solidified (FIG. 6F); and (7) air is pulled back or the well is physically flipped to drop the reagent(s) (FIG. 6G).

The method described herein, in one implementation, may further include exposing the composition to a second release-condition to release at least one reagent, where the second release-condition is different from the first release condition.

The method described herein, in one implementation, may further include exposing the composition to a third release-condition to release at least one reagent, where the third release-condition is different from the first release condition and the second release condition.

Each of the reagents in the compositions described herein may respond to different release conditions. In certain implementations, a first, second, and/or third reagent may be in the microsphere matrix and may respond to different release conditions. In certain implementations, a first and third reagent respond to different release conditions. In certain implementations, a first and second reagent respond to different release conditions. In other implementations, a second and third reagent respond to different release conditions. Alternatively, a first, second, and/or third reagent may respond to the same or substantially similar release conditions. In certain implementations, a first and third reagent respond to the same or substantially similar release conditions. In certain implementations, a first and second reagent respond to the same or substantially similar release conditions. In certain implementations, a second and third reagent respond to the same or substantially similar release conditions.

The compositions, methods, cartridges, and systems described herein provide for timed-release so that various components and reagents may be released at different times, for example, in a sequential or otherwise controlled manner. The rate of release may be adjustable to allow for controlled-release of composition components and reagents. The rate of release may be for any suitable period of time. For example, a shell or an interior compartment of the lyophilised microspheres may release or dissolve over a short-period of time such as 1 minute or less (e.g., less than 1 second, 1 second, 10 seconds, 20 seconds, 30 seconds, 45 seconds, 60 seconds, or any period of time therebetween). Alternatively, a shell or an interior compartment of the lyophilised microspheres may release or dissolve over an intermediate-period of time such as between 1 minute and 30 minutes (e.g., 1 minute, 5 minutes, 10 minutes, 15 minutes, 20 minutes, 25 minutes, 30 minutes, or any period of time therebetween). Alternatively, a shell or an interior compartment of the lyophilised microspheres may release or dissolve over a long-period of time such as more than 30 minutes (e.g., 35 minutes, 40 minutes, 45 minutes, 50 minutes, 55 minutes, 60 minutes, 75 minutes, 90 minutes, 105 minutes, 120 minutes, more than 120 minutes, or any period of time therebetween). For example, a shell or an interior compartment of the lyophilised microspheres as described herein may release quickly (e.g., in under one minute) at a low pH (e.g., between about 2-6), while that same shell may release slowly (e.g., in about 30 or more minutes) at a high pH (e.g., between about 10-14). Likewise, a shell or an interior compartment of the lyophilised microspheres as described herein may release slowly (e.g., in about 30 or more minutes) at a low pH (e.g., between about 2-6), while that same shell may release quickly (e.g., in under one minute) at a high pH (e.g., between about 10-14). Similarly, a shell or interior compartment of the lyophilised microspheres as described herein may release quickly (e.g., in under one minute) at an elevated temperature (e.g., above about 25° C. or above about 40° C.), while that same shell or interior compartment may release slowly (e.g., in about 30 or more minutes) at a lower temperature (e.g., at or below about 25° C. or above about 40° C.). In another example, a shell or interior compartment of the lyophilised microspheres as described herein may release slowly (e.g., in about 30 or more minutes) at an elevated temperature (e.g., above about 25° C. or above about 40° C.), while that same shell or interior compartment may release quickly (e.g., in under one minute) at a lower temperature (e.g., at or below about 25° C. or above about 40° C.). In one implementation, either or both of the first and second conditions comprise a change in temperature. The temperature, for example, may be elevated to a temperature above about 25° C. or above about 40° C. Alternatively, the temperature, for example, may be reduced to at or below about 25° C. or above about 40° C.

As described herein, preventing release of the one or more reagent when the shell is exposed to a particular condition includes a prevention of release for at least an order of magnitude longer than under a different release condition. As described herein, preventing release of one or more reagent includes both complete prevention of reagent release and substantial delays in reagent release (i.e., preventing release of one or more reagent includes practically preventing release).

The compositions, methods, cartridges, and systems described herein may include, in the interior compartment, one or more dry reagent, one or more microsphere, one or more bead, one or more powder, one or more cake, one or more gel, one or more liquid, or any combination thereof.

The compositions and reagents described herein may include dry reagents and may optionally be lyophilised as, for example, a lyophilised microsphere. In one implementation, the composition includes a cake, a bead, or a powder. In another implementation, the composition may be a microsphere, a cake, or a combination thereof.

The composition described herein may exhibit mechanical rigidity. "Mechanical rigidity" of a bulk composition as used herein refers to a bulk composition that exhibits a loss of mass of up to 5%, more preferably up to 1%, even more preferably up to 0.5%, and most preferably up to 0.1% from the bulk composition after the bulk composition is subjected to mechanical stress such as vibration or shock stress. Maintaining mechanical rigidity of a bulk composition helps to reduce or prevent the loss of a lyophilised material during shipping. If, for example, a composition including lyophilised microspheres lacks mechanical stability, incomplete rehydration may occur, resulting in a loss of efficiency in a sequencing reaction. Incomplete rehydration could be caused by the unpredictable position of the lyophilized material where lyo fragments or shed powders might be located beyond the line of rehydration.

The composition may be any appropriate size or volume that is appropriate to prepare a wax-microsphere matrix that is suitable for sample preparation, sample extraction, library preparation, enrichment, clustering, sequencing, or any combination thereof. In one implementation, the composition has a volume of reagent in the matrix of between about 0.1 µL and about 100,000 µL. For example, the composition may have an active reagent volume of about 0.1 µL, 0.5 µL, 1 µL, 2 µL, 3 µL, 4 µL, 5 µL, 6 µL, 7 µL, 8 µL, 9 µL, 10 µL, 15 µL, 20 µL, 25 µL, 30 µL, 35 µL, 40 µL, 45 µL, 50 µL, 60 µL, 70 µL, 80 µL, 90 µL, 100 µL, 125 µL, 150 µL, 175 µL, 200 µL, 225 µL, 250 µL, 275 µL, 300 µL, 325 µL, 350 µL, 375 µL, 400 µL, 425 µL, 450 µL, 475 µL, 500 µL, 600 µL, 700 µL, 800 µL, 900 µL, 1,000 µL, 1,100 µL, 1,200 µL, 1,300 µL, 1,400 µL, 1,500 µL, 1,600 µL, 1,700 µL, 1,800 µL, 1,900 µL, 2,000 µL, 2,500 µL, 3,000 µL, 3,500 µL, 4,000 µL, 4,500 µL, 5,000 µL, 5,500 µL, 6,000 µL, 6,500 µL, 7,000 µL, 7,500 µL, 8,000 µL, 8,500 µL, 9,000 µL, 9,500 µL, 10,000 µL, 15,000 µL, 20,000 µL, 25,000 µL, 30,000 µL, 35,000 µL, 40,000 μL, 45,000 μL, 50,000 μL, 55,000 μL, 60,000 μL, 65,000 μL, 70,000 μL, 75,000 μL, 80,000 μL, 85,000 μL, 90,000 μL, 95,000 μL, 100,000 μL, or any volume between about 0.1 μL and about 100,000 μL. For example, the active reagent volume may be between about 1,000 μL and about 100,000 μL, between about 10,000 μL, and about 100,000 μL, between about 50,000 μL and about 100,000 μL, between about 0.1 μL and about 10,000 μL, between about 0.1 μL and about 50,000 μL, or any other suitable size.

The compositions described herein may include an additional reagent in the shell. In one implementation, the composition includes a reagent or additive in the shell. The reagent in the shell may include, for example, any of the foregoing reagents or additives. In one implementation, the shell contains no nucleic acid molecules, for example, the shell contains no DNA. In one implementation, the shell contains more than one reagent and, or in the alternative, more than one additive.

The compositions described herein may be used for multiple sequential co-assays comprising lysis, DNA analysis, RNA analysis, protein analysis, tagmentation, nucleic acid amplification, nucleic acid sequencing, DNA library preparation, SBS technology, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially. In one implementation, the composition is used for performing multiple co-assay reactions. The compositions, methods, cartridges, and systems described herein may, in one implementation, improve sequencing quality, enable one-pot library prep, and simplify manufacturing and use. As used herein, the term "one-pot reaction" may also be referred to as "transfer-free reaction."

The compositions, methods, cartridges, and systems described herein may be prepared for various stages of sequencing including, but not limited to, sample extraction, library preparation, enrichment, clustering, and sequencing. The composition may include any number of different reagents from those described herein or any reagent that may be useful in promoting utility of sequencing systems, for example, SBS technology.

In one implementation, a biological sample contacts the composition. A biological sample, may include, for example, whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. A biological sample can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., "Accurate Whole Human Genome Sequencing Using Reversible Terminator Chemistry," *Nature* 456:53-59 (2008) and WO/2013/131962, which are hereby incorporated by reference in their entirety.

Rehydration time will vary depending on composition content and reaction conditions (e.g., reagents, temperature, pH) as described herein. In one implementation, rehydration time may be between 0.1 seconds and 10 hours. For example, rehydration time may be about 0.1 seconds, 1 second, 10 seconds, 30 seconds, 45 seconds, 60 seconds, 5 minutes, 10 minutes, 12 minutes, 15 minutes, 20 minutes, 30 minutes, 40 minutes, 50 minutes, 60 minutes, 70 minutes, 80 minutes, 90 minutes, 2 hours, 5 hours, 8 hours, 10 hours, or any amount of time therebetween.

A rehydration (or reconstitution) solution as used herein may include water, deionized water, saline solutions, acidic solutions, basic solutions, detergent solutions and/or buffers, and may be in accordance with rehydration solutions previously described. In one implementation, the rehydration solution is water, ethanolamine, or a combination thereof. In one implementation, reagents described herein having varying concentrations, types of enzymes, and different amounts of co-factors, salts, pHs, and more, can be rehydrated with water alone, or even atmospheric water capture. Additional additives as described herein may be provided in the rehydration solution.

In one implementation, the method further includes flowing the rehydrated composition (e.g., at least one rehydrated lyophilised microsphere) or the one or more reagent through a flow cell. In one implementation, the method further includes flowing the rehydrated composition (e.g., at least one rehydrated lyophilised microsphere) or the one or more reagent during a sequencing by synthesis process. In another implementation, the method further includes exposing the rehydrated composition to a sequencing primer, where incorporation of the one or more modified nucleotide in the sequencing primer generates an extended sequencing primer. In another implementation, the method further includes applying the rehydrated composition to a solid support comprising a nucleotide cluster, where the nucleotide cluster comprises a target polynucleotide.

A second aspect relates to a method of preparing a wax-microsphere matrix. The method includes mixing a plurality of lyophilised microspheres, wherein said plurality of lyophilised microspheres comprise one or more reagent, with a wax component under conditions effective to form a wax-microsphere matrix.

This aspect may be in accordance with the previously described aspect.

In one implementation, the wax-microsphere matrix comprises a random distribution of the plurality of lyophilised microspheres. In another implementation, the wax-microsphere matrix comprises a uniform distribution of the plurality of lyophilised microspheres.

In one implementation, the wax-microsphere matrix is at a temperature of above about 40° C. For example, the mixing may be occur at a temperature between about 40° C. and about 41° C., about 41° C., about 42° C., about 43° C., about 44° C., about 45° C., about 50° C., about 55° C., about 60° C., about 65° C., about 70° C., about 75° C., about 80° C., about 85° C., about 90° C., about 95° C., about 100° C., above about 100° C., or any temperature suitable to achieve melt of the wax component.

In one implementation, lowering the temperature of the wax-microsphere matrix is conducted to solidify the wax-microsphere matrix. In one implementation, the lowering of temperature of the wax-microsphere matrix comprises a lowering of the temperature to at or below about 40° C. The temperature in the modification may be, for example, between about 0° C. and about 40° C., about 39° C., about 38° C., about 37° C., about 36° C., about 35° C., about 34° C., about 33° C., about 32° C., about 31° C., about 30° C., about 25° C., about 24° C., about 23° C., about 22° C., about 21° C., about 20° C., about 19° C., about 18° C., about 17° C., about 16° C., about 15° C., about 10° C., about 5° C., about 4° C., about 3° C., about 2° C., about 1° C., about 0°

C., below about 0° C., or any temperature suitable to achieve solidification of the wax component.

Figure 2A:
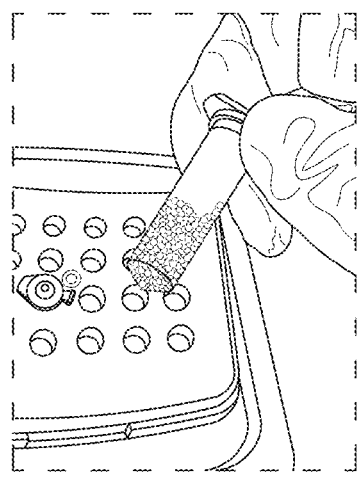
FIGS. 2A-2C show production of wax slugs containing microspheres.
Figure 2B:
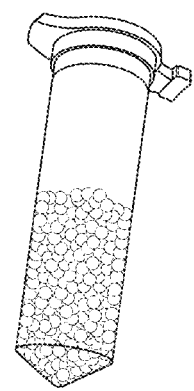

The wax-microsphere matrix composition (i.e., wax slugs containing microspheres) may be produced by combining microspheres with melted wax (for example, a molten paraffin wax). The microspheres and melted wax may be placed on a thermomixer at 1000 rpm to keep the microspheres in suspension. The temperature may be dropped to 40° C. to solidify wax while mixing, thereby forming a wax slug, as shown in FIGS. 2A and 2B. The extracted wax slug containing microspheres using this production process is shown in FIG. 2C.

Figure 2C:
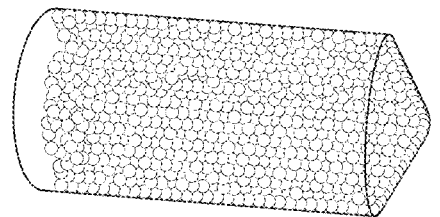

Wax slugs maybe prepared by dispensing dry microspheres into a well plate, dispensing wax in a liquid state (warm) or dry state (cold), shaking the well plate at a warm temperature, centrifuging plate at warm temperature, shaking plate at warm temperature, and setting plate at room temperature, followed by the plate being dropped or flipped to extract the slug, as shown in FIGS. 2A-2C.

Figure 12:
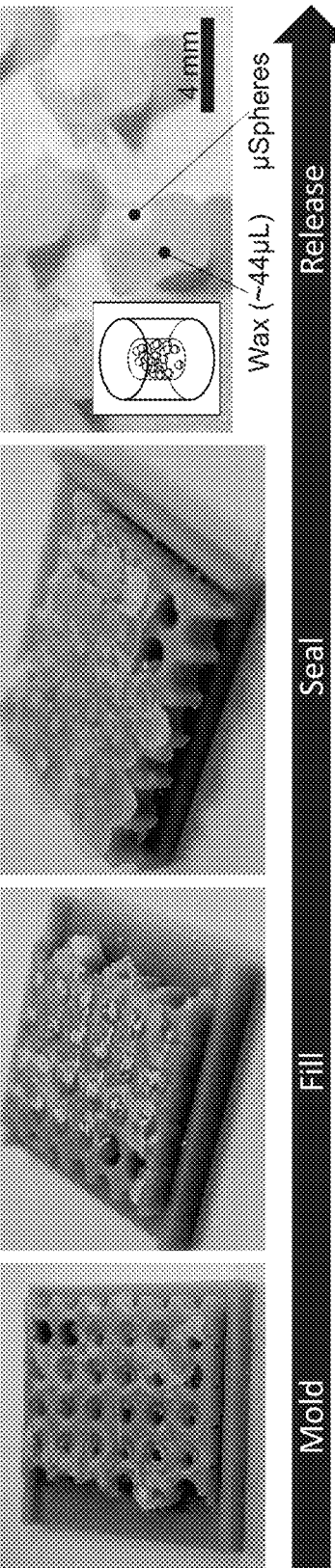
FIG. 12 shows an example method of production of a wax-microsphere matrix with a cavity by using a mold.

A method of preparing a wax-microsphere matrix may further include forming a wax component in a mold, the wax component including a cavity; and sealing the cavity with wax after the mixing (FIG. 12). In an implementation, the mold includes a plurality of wells, and each well is filled with hot wax. For example, each well of the mold may be filled with about 40 µL to about 50 µL of hot wax, including any and all subranges therein, e.g., about 40.1 µL, about 40.2 µL, about 40.3 µL, about 40.4 µL, about 40.5 µL, about 41 µL, about 42 µL, about 43 µL, about 44 µL, about 45 µL, about 46 µL, about 47 µL, about 48 µL, about 49 µL, and about 50 µL. In another implementation, while the wax in each well of the mold is hot, pins may be pushed into each well and the wax is cooled before removing the pins to create the cavity. The cavity may have a volume in the range of about 10 µL to about 80 µL, including any and all subranges therein, e.g., about 11 µL, about 12 µL, about 13 µL, about 14 µL, about 15 µL, about 16 µL, about 17 µL, about 18 µL, about 19 µL, about 20 µL, about 25 µL, about 30 µL, about 40 µL, about 50 µL, about 60 µL, about 70 µL, and about 80 µL, etc.

Figure 13:
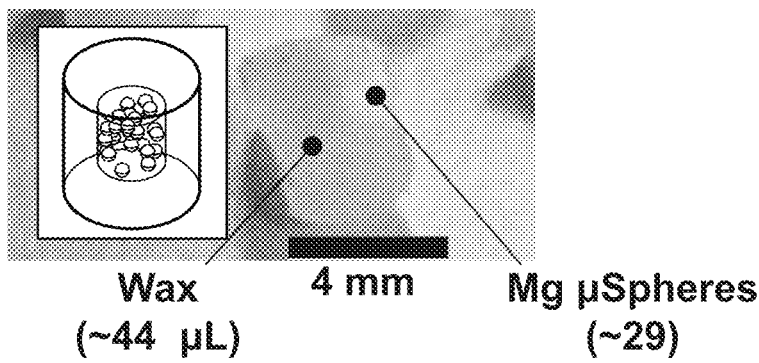
FIG. 13 shows an example of a wax-microsphere matrix with a cavity made using a mold.

In an implementation, mixing may include filling the cavity with the plurality of lyophilised microspheres. In another implementation, the cavity may be filled with microspheres. The number of microspheres that may fit in the cavity may depend on the geometry of the microspheres or the size of the cavity. For example, the cavity may be filled with about 1, about 2, about 3, about 4, about 5, about 6, about 7, about 8, about 9, about 10, about 15, about 20, about 25, about 30, about 40, about 50, or about 60 microspheres, etc. In yet another implementation, after the cavity is filled with microspheres, the cavity may be sealed with wax. For example, hot liquid wax may be pressed into a flat sheet on top of the mold. In still another implementation, the wax-microsphere matrix may be cooled and separated from the mold. An example of a wax-microsphere matrix is shown in FIG. 13, where the wax component includes about 44 µL of paraffin wax and the cavity is filled with approximately 29 microspheres.

A third aspect relates to a composition. The composition includes a wax-microsphere matrix, said wax-microsphere matrix comprising: a wax component and a plurality of lyophilised microspheres, wherein said plurality of lyophilised microspheres comprise one or more reagent.

This aspect may be in accordance with the previously described aspects.

A fourth aspect relates to a method. The method includes elevating a temperature of a composition comprising a wax-microsphere matrix in a well from a first temperature to a second temperature; flowing a liquid in said well; mixing said composition and said liquid in said well; and lowering the temperature of said liquid from the second temperature to a third temperature under conditions effective to release one or more reagent from said wax-microsphere matrix.

This aspect may be carried out in accordance with the previously described aspects.

In one implementation, the wax-microsphere matrix comprises the composition of described herein.

In one implementation, the second temperature is above about 40° C. as described herein. For example, the second temperature may be between about 40° C. and about 41° C., about 41° C., about 42° C., about 43° C., about 44° C., about 45° C., about 50° C., about 55° C., about 60° C., about 65° C., about 70° C., about 75° C., about 80° C., about 85° C., about 90° C., about 95° C., about 100° C., above about 100° C., or any temperature suitable to achieve melt of the wax component. In one implementation, the second temperature releases at least one reagent as described herein. In one implementation, the second temperature releases the interior compartment.

In one implementation, the third temperature is at or below about 40° C. In one implementation, the third temperature may be, for example, between about 0° C. and about 40° C., about 39° C., about 38° C., about 37° C., about 36° C., about 35° C., about 34° C., about 33° C., about 32° C., about 31° C., about 30° C., about 25° C., about 24° C., about 23° C., about 22° C., about 21° C., about 20° C., about 19° C., about 18° C., about 17° C., about 16° C., about 15° C., about 10° C., about 5° C., about 4° C., about 3° C., about 2° C., about 1° C., about 0° C., below about 0° C., or any temperature suitable to achieve solidification of the wax component. In one implementation, the first temperature is different from the third temperature. In one implementation, the first temperature is the same as the third temperature.

In one implementation, the mixing further comprises addition of an aqueous solution in the well. In one implementation, the mixing comprises mixing the composition and the aqueous solution.

In one implementation, the method further includes exposing the composition to one or more additional temperature modifications to release at least one reagent, wherein the one or more additional temperature modifications are to a temperature that is different from the second temperature. In one implementation, the method further includes exposing the composition to one or more additional temperature modifications to release at least one reagent, wherein the one or more additional temperature modifications are to a temperature that is different from the third temperature. The additional temperature modifications may elevate or lower the temperature and may be higher than or lower than the first, second, and/or third temperature.

In one implementation, the method further includes removing the wax component after releasing one or more reagent from the wax-microsphere matrix. This step may be carried out in accordance with the previously described aspects.

In one implementation, the method further includes using the at least one rehydrated lyophilised microsphere or the one or more reagent in a sequencing by synthesis process. For example, the at least one rehydrated lyophilised microsphere or the one or more reagent may be flowed through a flow cell.

A fifth aspect relates to a cartridge. The cartridge includes a reagent reservoir, the reagent reservoir comprising a wax-microsphere matrix composition, said wax-microsphere matrix composition comprising a wax component and a plurality of lyophilised microspheres, wherein said plurality of lyophilised microspheres comprise one or more reagent.

This aspect may be carried out in accordance with the previously described aspects.

Exemplary cartridges and configurations are described in, for example, U.S. Pat. No. 8,637,242, which is hereby incorporated by reference in its entirety. Exemplary flow cells are described, for example, in U.S. Pat. No. 8,241,573, which is hereby incorporated by reference in its entirety.

Additionally or alternatively, a cartridge can include separate reservoirs and fluidic systems used to carry out amplification methods and to carry out detection methods. Examples of integrated sequencing systems that are capable of creating amplified nucleic acids and also determining the sequence of the nucleic acids include, without limitation, the MiSeg™ platform (Illumina, Inc., San Diego, CA) and devices described in U.S. Pat. No. 8,951,781, which is hereby incorporated by reference in its entirety.

In one implementation, the cartridge further includes a plurality of wax-microsphere matrix compositions in the reagent reservoir.

A sixth aspect relates to a system for controlling release of one or more reagent. The system includes a well; a wax-microsphere matrix composition, said wax-microsphere matrix composition comprising a wax component and a plurality of lyophilised microspheres, wherein said plurality of lyophilised microspheres comprise one or more reagent; and a liquid.

This aspect may be carried out in accordance with the previously described aspects.

The liquid as described herein may be present in the well or, alternatively, the composition may be present in the well. In one implementation, the liquid is in the well. In another implementation, the composition is in the well.

The system may further include a temperature controller or sensor. The temperature controller may be used to change or adjust temperature of the system to further control conditions described herein. For example, the temperature controller may be used to speed up or slow down the melt-condition, one or more release-condition, and/or separation-condition. In one implementation, the system comprises a temperature controller on the well. For example, the temperature controller may include a resistive heater proximate to a wall of the well to provide heat thereto. The temperature controller may also include a temperature sensor. The temperature controller may also include circuitry to activate and deactivate the heater to maintain the well at a specified temperature.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

In the present disclosure, reference is made to the accompanying drawings that form a part hereof, and in which is shown by way of illustration specific implementations which may be practiced. These implementations are described in detail to enable those skilled in the art to practice the disclosure, and it is to be understood that other implementations may be utilized and that structural, logical and electrical changes may be made without departing from the scope of the present disclosure. The following description of example implementations is, therefore, not to be taken in a limited sense.

The present disclosure may be further illustrated by reference to the following examples.

EXAMPLES

The following examples are intended to illustrate, but by no means are intended to limit, the scope of the present disclosure as set forth in the appended claims.

Example 1—Improvement by Matrix Bulk Encapsulation of Microspheres in Wax

Figure 1B:
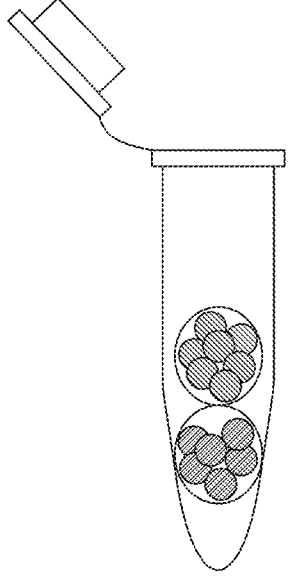

FIGS. 1A-1B show improvement and mitigation of existing microsphere usage with wax slugs containing microspheres described herein. FIG. 1A shows current state microspheres which are scattered throughout the well by electrostatic cling. Thus, microspheres are located on sides and top of wells and the well needs washing of the sides and top. FIG. 1B shows improvement with use of wax slugs containing microspheres described herein.

Example 2—Method of Making Matrix Bulk Encapsulation of Microspheres in Wax Wax slugs containing microspheres may be produced by combining microspheres with melted wax (for example, a molten paraffin wax). The microspheres and melted wax are placed on a thermomixer at 1000 rpm to keep the microspheres in suspension. The temperature is dropped to 40° C. to solidify wax while mixing, thereby forming a wax-microsphere matrix composition (e.g., a wax slug), as shown in FIGS. 2A and 2B. The wax slug containing microspheres is extracted as shown in FIG. 2C.

Wax slugs may also be prepared by dispensing dry microspheres into a well plate, dispensing wax in a liquid state (warm) or dry state (cold), shaking the well plate at a warm temperature, centrifuging the plate at a warm temperature, shaking the plate at a warm temperature, and setting the plate at room temperature, followed by dropping or flipping the plate to extract the slug. This process is shown in FIGS. 2A-2C.

Figure 3:
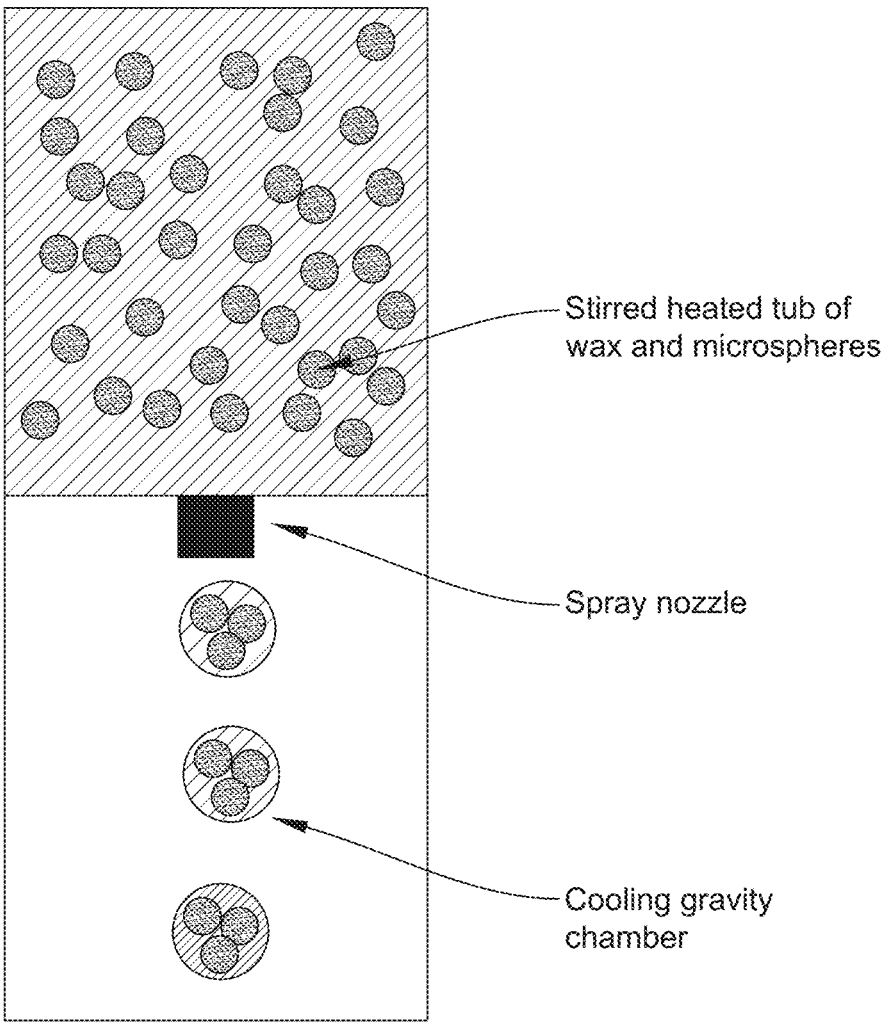
FIG. 3 shows a method of production of a wax slug containing microspheres in accordance with the present disclosure.

FIG. 3 shows a process for making wax slugs described herein, which shows mixing of microspheres with wax in a large container, creating droplets that solidify as they gravitate down a cooling tower.

Example 3—Composition of Matrix Bulk Encapsulation of Microspheres in Wax

Figure 4:
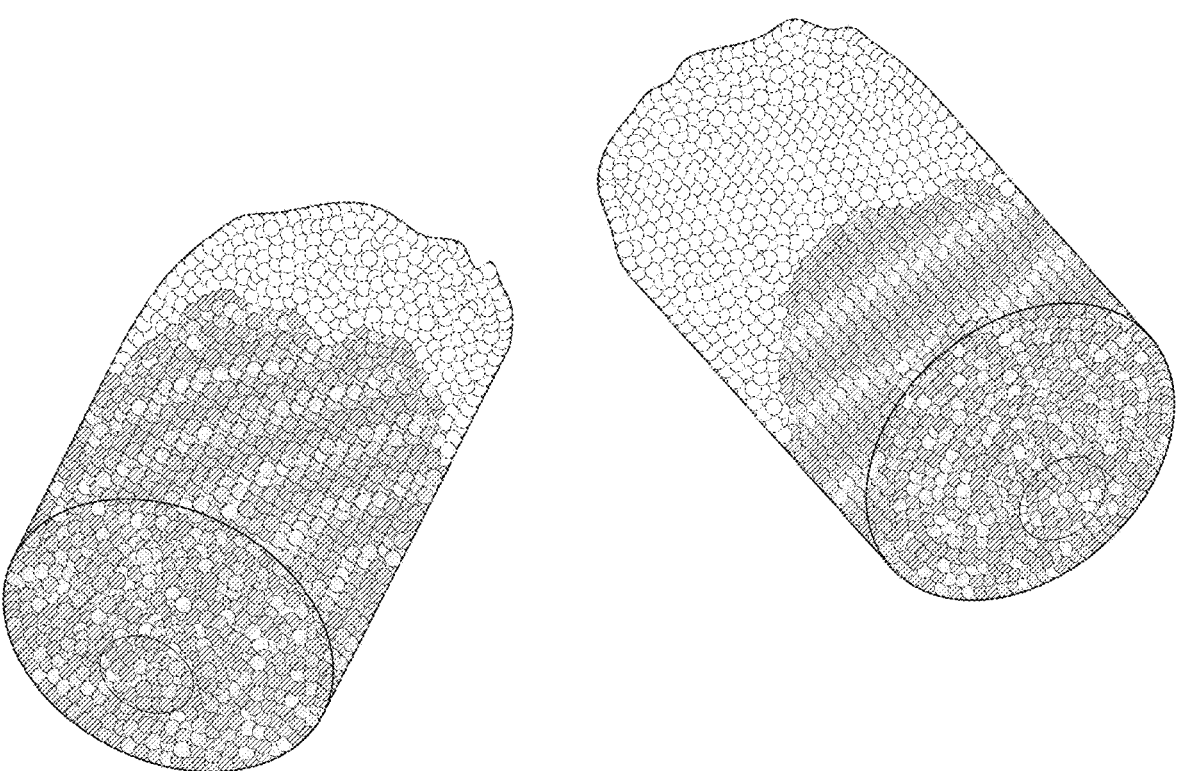
FIG. 4 shows an example of the wax-microsphere matrix composition (e.g., wax slug) described herein that is composed of two types of microspheres.

An example of a matrix bulk encapsulation of microspheres in wax (i.e., the wax-microsphere matrix composition) is shown in FIG. 4. The matrix may include one or more than one type of microsphere. As shown in FIG. 4, when there are a plurality of microsphere types in a wax slug, those microspheres may be separated based on type. Alternatively, the plurality of microsphere types, when present, may be distributed throughout the wax slug.

Example 4—Method of Rehydration of Wax-Microsphere Matrix

FIGS. 5A-5E show an example of a method of rehydration of the wax-microsphere composition described herein. FIG. 5A shows a wax-microsphere matrix composition at about 20° C. FIG. 5B shows the wax-microsphere matrix at about 70° C. FIG. 5C shows the wax-microsphere matrix composition at about 70° C. after water is added, with the wax being found at the top of the composition and microspheres being rehydrated. FIG. 5D shows the wax-microsphere matrix composition after rehydration and at about 20° C. with the wax being located at the top of the composition. FIG. 5E shows the separation of the wax and reagent that is released upon rehydration of the microspheres from the wax-microsphere matrix composition.

FIGS. 6A-6G show an example of a method of rehydration of the wax microsphere-matrix composition described herein. FIG. 6A shows a wax-microsphere matrix composition described herein (e.g., a "slug" or "wax slug") inside a tube. FIG. 6B shows melting of the wax component of the wax-microsphere matrix composition. FIG. 6C shows addition of rehydration buffer to the melted wax-microsphere matrix composition. FIG. 6D shows mixing of the melted wax component of the wax-microsphere matrix composition to mix rehydrated microspheres. FIG. 6E shows one example of moving the wax component, by pushing the solution up with air (or physically flipping the well). FIG. 6F shows solidification of wax. FIG. 6G shows pulling back of air to drop the reagent(s) (which may alternatively be achieved by physically flipping the well).

Figure 7:
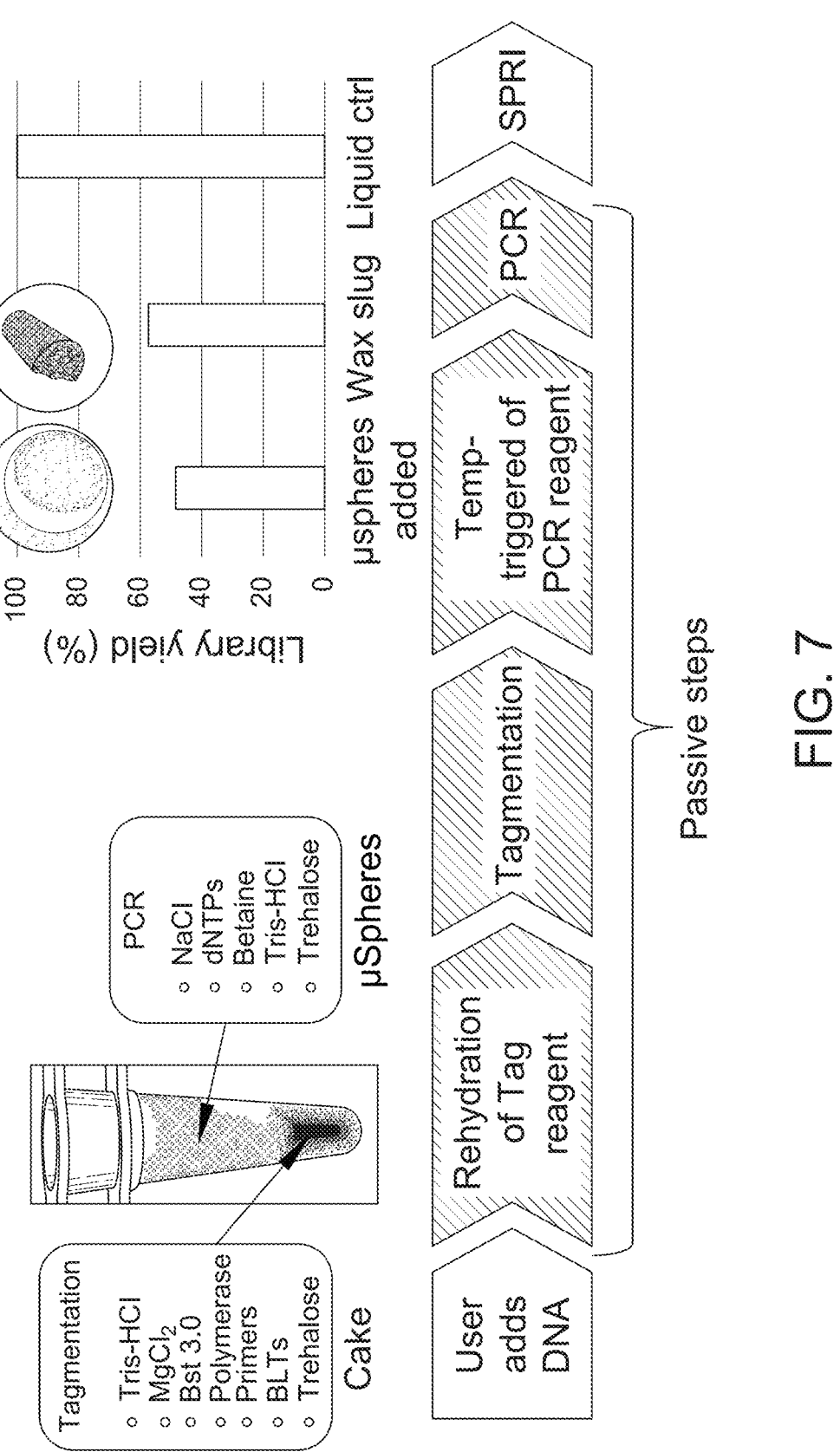
FIG. 7 shows examples of applications and reagents that may be used in accordance with the methods, compositions, cartridges, and systems described herein.

FIG. 7 shows examples of applications and reagents that may be used in accordance with the methods, compositions, cartridges, and systems described herein.

Figure 8:
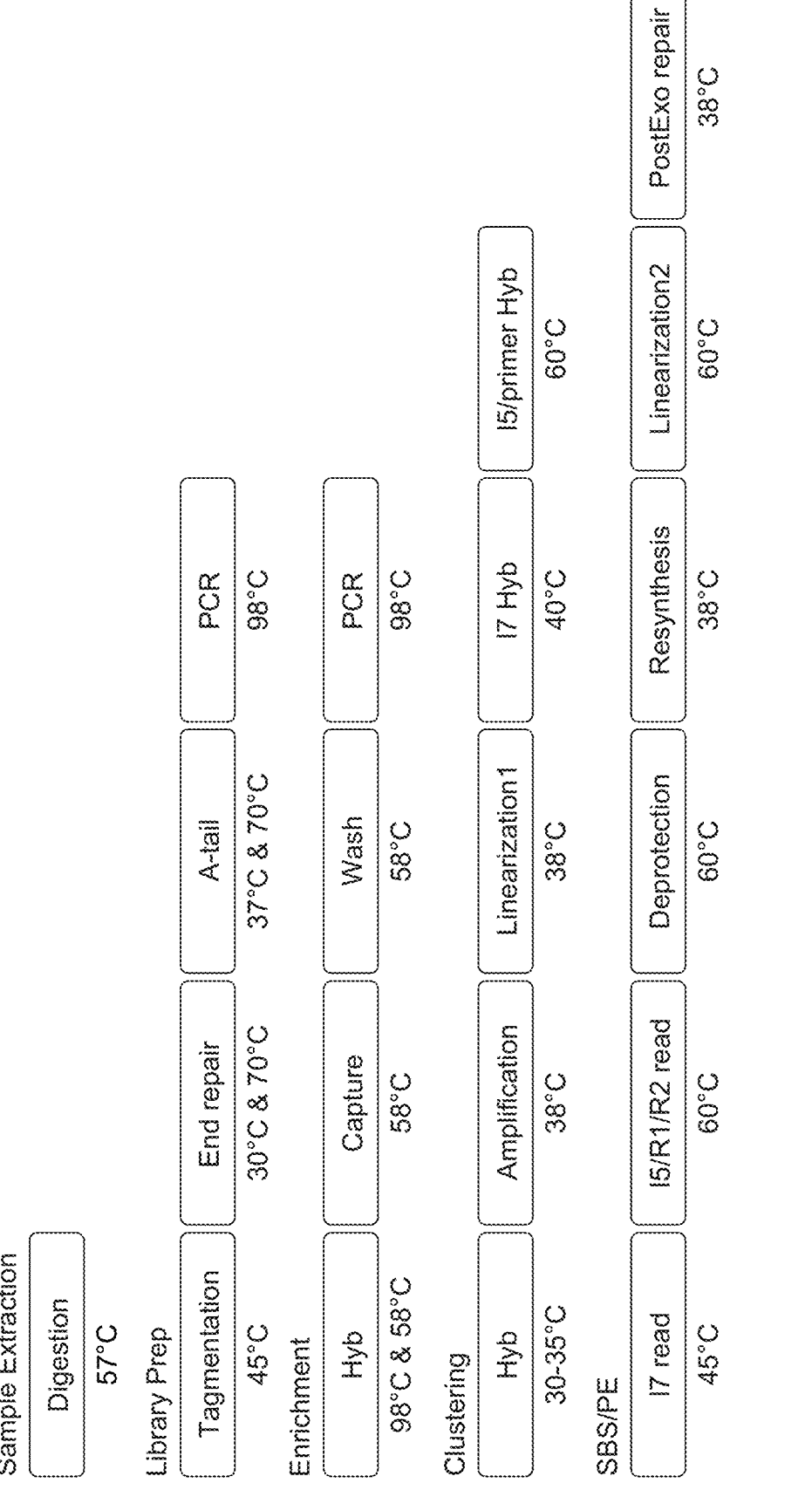
FIG. 8 shows examples of applications and reagents that may be used in accordance with the methods, compositions, cartridges, and systems described herein.

FIG. 8 shows a examples of applications and reagents that may be used in accordance with the methods, compositions, cartridges, and systems described herein.

FIG. 9 shows a flow chart describing one aspect described herein for a method. The method includes exposing a composition comprising a wax-microsphere matrix to a first melt-condition, wherein the wax-microsphere matrix comprises a wax component and a plurality of lyophilised microspheres, wherein the plurality of lyophilised microspheres comprise one or more reagent, whereby exposing the composition comprising the wax-microsphere matrix to the first melt-condition melts the wax component; exposing the composition to a first release-condition to rehydrate at least one lyophilised microsphere; and exposing the rehydrated lyophilised microsphere to a separation-condition to separate the wax component from the rehydrated lyophilised microsphere.

FIG. 10 shows a flow chart describing one aspect described herein for a method of preparing a wax-microsphere matrix. The method includes mixing a plurality of lyophilised microspheres, wherein the plurality of lyophilised microspheres comprise one or more reagent, with a wax component under conditions effective to form a wax-microsphere matrix.

Figure 11:
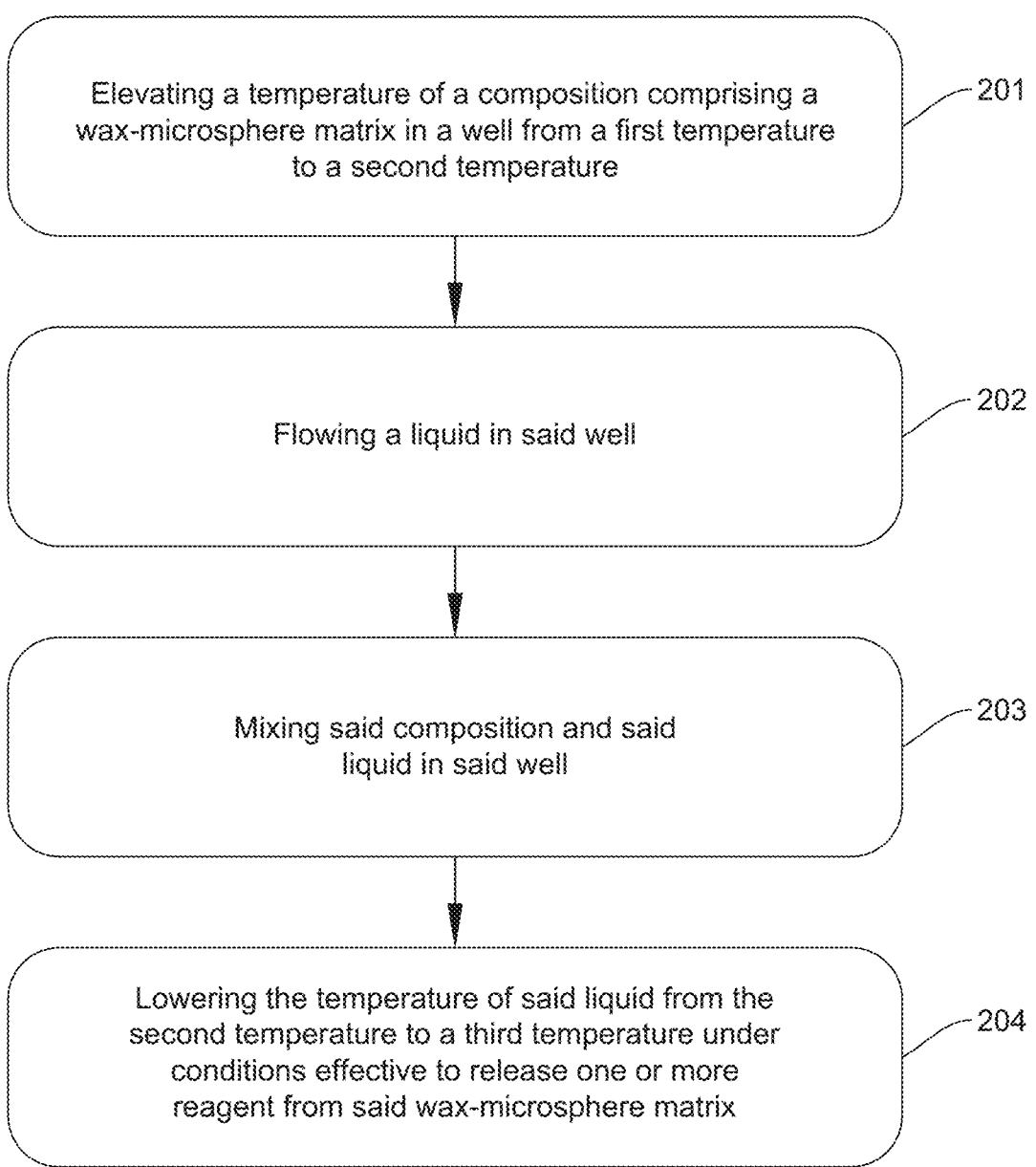
FIG. 11 shows a flow chart describing one aspect described herein for a method.

FIG. 11 shows a flow chart describing one aspect described herein for a method. The method includes elevating a temperature of a composition comprising a wax-microsphere matrix in a well from a first temperature to a second temperature; flowing a liquid in the well; mixing the composition and the liquid in the well; and lowering the temperature of the liquid from the second temperature to a third temperature under conditions effective to release one or more reagent from the wax-microsphere matrix.

Although preferred implementation have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

Example 5—Method of Making a Wax-Microsphere Matrix with a Cavity

In an example, a wax-microsphere matrix with a cavity was made by filling the wells of a mold with hot wax, pushing pins into each well while the wax was hot, cooling the wax, and removing the pins to create a cavity in each well. The cavities were filled with microspheres and the filled cavities sealed with additional hot liquid wax pressed into a flat sheet at the top of each cavity. Upon cooling the assembly was separated to release each wax-microsphere matrix containing microspheres (FIG. 12). An example of a wax-microsphere matrix with a cavity filled with lyophilised microspheres is shown in FIG. 13. In the example in FIG. 13, the wax component includes about 44 μL of paraffin wax and the cavity is filled with approximately twenty-nine (29) microspheres.

What is claimed:

1. A method comprising:
exposing a composition comprising a wax-microsphere matrix to a first melt-condition, wherein said wax-microsphere matrix comprises a wax component and a plurality of lyophilised microspheres, wherein said plurality of lyophilised microspheres comprise one or more reagent, whereby exposing said composition comprising said wax-microsphere matrix to said first melt-condition melts the wax component;
exposing said composition to a first release-condition to rehydrate at least one lyophilised microsphere;
exposing said at least one rehydrated lyophilised microsphere to a separation-condition to separate said wax component from said at least one rehydrated lyophilised microsphere, wherein said separation-condition comprises a temperature at or below about 40° C.

2. The method of claim 1, wherein said first melt-condition comprises a temperature of above about 40° C.

3. The method of claim 1, wherein said first release-condition comprises mixing said composition with an aqueous solution.

4. The method of claim 1, wherein at least one of said plurality of lyophilised microspheres comprise a shell surrounding an interior compartment, wherein said interior compartment comprises the one or more reagent.

5. The method of claim 1, wherein said one or more reagent comprises a sample preparation reagent, a sample extraction reagent, a library preparation reagent, an enrichment reagent, a clustering reagent, a sequencing reagent, or any combination thereof.

6. The method of claim 1, wherein said one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof.

7. The method of claim 1, further comprising using the at least one rehydrated lyophilised microsphere in a sequencing by synthesis process.

8. The method of claim 1, further comprising using the at least one rehydrated lyophilised microsphere in a library preparation process.

9. The method of claim 1, further comprising using the at least one rehydrated lyophilised microsphere in a sample preparation process.

10. The method of claim 1, wherein said wax component comprises a wax selected from spermaceti, Japan wax, paraffin, ceresin, ozocerite, bees wax, candelilla, montan, barnsdahl, ouricury, carnauba, or any combination thereof.

11. A composition comprising:

a wax-microsphere matrix, said wax-microsphere matrix comprising: a wax component and a plurality of lyophilised microspheres, wherein said plurality of lyophilised microspheres comprise one or more reagent, said one or more reagent comprising: a sample preparation reagent, a sample extraction reagent, a library preparation reagent, an enrichment reagent, a clustering reagent, a sequencing reagent, or any combination thereof.

12. The composition of claim 11, wherein at least one of said plurality of lyophilised microspheres comprise a shell surrounding an interior compartment, wherein said interior compartment comprises the one or more reagent.

13. The composition of claim 11, wherein said one or more reagent comprises two or more of said reagents.

14. The composition of claim 11, wherein said one or more reagent is selected from one or more enzyme, salt, surfactant, buffering agent, enzyme inhibitor, primer, nucleotide, organic osmolite, magnetic bead, molecular probe, crowding agent, small molecule, labelled-nucleotide, or any combination thereof.

15. The composition of claim 11, wherein said wax component comprises a wax selected from spermaceti, Japan wax, paraffin, ceresin, ozocerite, bees wax, candelilla, montan, barnsdahl, ouricury, carnauba, or any combination thereof.

16. A cartridge comprising:

a reagent reservoir, the reagent reservoir comprising a wax-microsphere matrix composition according to claim 11.

17. A system for controlling release of one or more reagent comprising:

a well;

a wax-microsphere matrix composition, said wax-microsphere matrix composition comprising a wax component and a plurality of lyophilised microspheres, wherein said plurality of lyophilised microspheres comprise one or more reagent, said one or more reagent comprising: a sample preparation reagent, a sample extraction reagent, a library preparation reagent, an enrichment reagent, a clustering reagent, a sequencing reagent, or any combination thereof; and a liquid.

18. The system of claim 17, wherein one or more of (i) said liquid is in said well and (ii) said composition is in said well.

19. The system of claim 17, further comprising:

a temperature controller on said well.

* * * * *